US012245782B2

(12) United States Patent
Nguyen et al.

(10) Patent No.: US 12,245,782 B2
(45) Date of Patent: *Mar. 11, 2025

(54) SHOCK WAVE ELECTRODES

(71) Applicant: Shockwave Medical, Inc., Santa Clara, CA (US)

(72) Inventors: Hoa D. Nguyen, San Jose, CA (US); John M. Adams, Snohomish, WA (US)

(73) Assignee: SHOCKWAVE MEDICAL, INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/755,486

(22) Filed: Jun. 26, 2024

(65) Prior Publication Data
US 2024/0341787 A1 Oct. 17, 2024

Related U.S. Application Data

(62) Division of application No. 17/725,435, filed on Apr. 20, 2022, now Pat. No. 12,064,129, which is a
(Continued)

(51) Int. Cl.
A61B 17/22 (2006.01)
(52) U.S. Cl.
CPC .... A61B 17/2202 (2013.01); A61B 17/22022 (2013.01); A61B 2017/22001 (2013.01);
(Continued)
(58) Field of Classification Search
CPC ........... A61B 2017/00526; A61B 2017/00595; A61B 2017/00606
See application file for complete search history.

(56) References Cited

U.S. PATENT DOCUMENTS 2,916,647 A 12/1959 George
3,412,288 A 11/1968 Ostrander
(Continued)

FOREIGN PATENT DOCUMENTS

AU 2009313507 B2 11/2014
AU 2013284490 B2 5/2018
(Continued)

OTHER PUBLICATIONS

Abraham et al. (1992). "Effect of Humidity and on the dc Breakdown and Rod-Plane Temperature of Rod-Rod Gaps," IEEE Transactions on Electrical Insulation, 27(2):207-213.
(Continued)

Primary Examiner — Alexander J Orkin
(74) Attorney, Agent, or Firm — Morrison & Foerster LLP

(57) ABSTRACT

Disclosed herein shock wave catheters comprising one or more shock wave electrodes for cracking calcifications located within blood vessels. In some variations, a shock wave catheter has first and second shock wave electrodes each circumferentially disposed over the outer surface of the catheter. In certain variations, the first electrode has a recess and the second electrode has a protrusion that is received by the recess and a spark gap is located along the separation between the recess and the protrusion. The second electrode can also have a recess that receives a protrusion from a third shock wave electrode, where the separation between the second and third electrodes along the separation between the recess and the protrusion forms a second spark gap. A shock wave can be initiated across these spark gaps when a voltage is applied over the electrodes.

17 Claims, 9 Drawing Sheets

Related U.S. Application Data division of application No. 16/691,449, filed on Nov. 21, 2019, now Pat. No. 11,337,713, which is a division of application No. 15/346,132, filed on Nov. 8, 2016, now Pat. No. 10,555,744.

(60) Provisional application No. 62/257,141, filed on Nov. 18, 2015.

(52) U.S. Cl.
CPC .............. *A61B 2017/22021* (2013.01); *A61B 2017/22025* (2013.01); *A61B 2017/22061* (2013.01)

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzel |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,103,360 B2 | 1/2012 | Foster |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |

(56) References Cited

U.S. PATENT DOCUMENTS

| | | |
|---|---|---|
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall |
| 2012/0157991 A1 | 6/2012 | Christian |
| 2012/0203255 A1 | 8/2012 | Hawkins et al. |
| 2012/0253358 A1 | 10/2012 | Golan |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0005576 A1 | 1/2014 | Adams et al. |
| 2014/0039513 A1 | 2/2014 | Hakala et al. |
| 2014/0046229 A1 | 2/2014 | Hawkins et al. |
| 2014/0052147 A1* | 2/2014 | Hakala ............ A61B 17/22022 606/128 |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2020/0085458 A1 | 3/2020 | Nguyen et al. |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0293197 A1 | 9/2023 | Nguyen et al. |
| 2023/0310073 A1 | 10/2023 | Adams et al. |
| 2023/0329731 A1 | 10/2023 | Hakala et al. |
| 2023/0380849 A1 | 11/2023 | Adams et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | 1099444 A | 4/1998 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |

(56) References Cited

FOREIGN PATENT DOCUMENTS

| | | |
|---|---|---|
| JP | 2005501597 A | 1/2005 |
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011520248 A | 7/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A3 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |

OTHER PUBLICATIONS

Advisory Action received for U.S. Appl. No. 12/482,995, mailed on Jun. 2, 2014, 3 pages.
Advisory Action received for U.S. Appl. No. 12/482,995, mailed on Sep. 29, 2011, 2 pages.
Advisory Action received for U.S. Appl. No. 12/581,295, mailed on Jul. 3, 2014, 3 pages.
Advisory Action received for U.S. Appl. No. 13/049,199, mailed on Jun. 7, 2012, 3 pages.
Advisory Action received for U.S. Appl. No. 13/267,383, mailed on Jan. 6, 2014, 4 pages.
Advisory Action received for U.S. Appl. No. 13/615,107, mailed on Nov. 6, 2015, 3 pages.
Allen et al. (1993). "Dielectric Breakdown in Nonuniform Field Air Gaps: Ranges of Applicability to dc Voltage Measurement," IEEE Transactions on Electrical Insulation, 28(2):183-191.
Allibone et al. (1972). "Influence of Humidity on the Breakdown of Sphere and Rod Gaps Under Impulse Voltages of Short and Long Wavefronts," Proceedings of the Institution of Electrical Engineers, 119(9):1417-1422.
Amighi et al. (2005). "Impact of the Rapid-Exchange Versus Over-the-Wire Technique on Procedural Complications of Renal Artery Angioplasty," J Endovasc Ther., vol. 12, pp. 233-239.
Anvari et al. (1973). "Study of a 40 KV Multistage Spark Gap Operated in Air at Atmospheric Pressure," Exhibit 1044, Declaration of Juanita DeLoach, Ph.D., 3 pages.

Armstrong, Ehrin, "Responses to Question 6 by Patent Owner's Declarants Ehrin Armstrong," Jan. 29, 2020, 5 pages.
Armstrong, Ehrin, "Responses to Questions 1-5 by Patent Owner's Declarants Ehrin Armstrong," Jan. 24, 2020, 4 pages.
Athanasoulis (1980). "Percutaneous Transluminal Angioplasty: General Principles," American journal of Roentgenology, vol. 135, pp. 893-900.
Bank of America Merrill Lynch, "A Simple Solution to a Difficult (and Large) Problem—Initiating Coverage of SWAV," Shockwave Medical Inc., Apr. 1, 2019, pp. 1-22.
Becker et al. (1988). "Radiofrequency Balloon Angioplasty. Rationale and Proof of Principle," Investigative Radiology, 23(11):810-817.
Belmouss (2015). "Effect of Electrode Geometry on High Energy Spark Discharges in Air," Purdue University Open Access Theses, 216 pages.
Bittl et al. (1993). "Coronary Artery Perforation during Excimer Laser Coronary Angioplasty," Journal of the American College of Cardiology, 21(5):1158-1165.
Bittl et al. (1993). "Publication Information—Coronary Artery Perforation during Excimer Laser Coronary Angioplasty," Journal of the American College of Cardiology, 21(5):1-6.
Brace et al. (2009). "Pulmonary Thermal Ablation: Comparison of Radiofrequency and Microwave Devices by Using Gross Pathologic and CT Findings in a Swine Model," Radiology, 251(3):705-711.
Brinton et al. (2016). "Publication Information—TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68, No. 18, Supplement, pp. 1-5.
Brinton et al. (2016). "TCT-777 Safety and Performance of the Shockwave Medical Lithoplasty® System in Treating Calcified Peripheral Vascular Lesions: 6-Month Results from the Two-Phase Disrupt Pad Study," Journal of the American College of Cardiology, 68, No. 18, Supplement B, p. B314.
Cardiology Today's Intervention, "Shockwave Attracts Additional Investment from Abiomed, has IPO," Available Online at <https://www.healio.com/cardiac-vascular-intervention/peripheral/news/online/%7Bf96c1e20-b4a9-4167-bdb8-254e86a8182a%7D/shockwave-attracts-additional-investment-from-abiomed-has-ipo>, Mar. 12, 2019, pp. 1-2.
Cleveland et al. (2000). "Design and Characterization of a Research Electrohydraulic Lithotripter Patterned after the Dornier HM3," Review of Scientific Instruments, 71(6):2514-2525.
Cleveland et al. (2000). "Publication Information—Design and Characterization of a Research Electrohydraulic Lithotripter Patterned after the Dornier HM3," Review of Scientific Instruments, 71, No. 6, 4 pages.
Cleveland et al. (2012). "The Physics of Shock Wave Lithotripsy," Extracorporeal Shock Wave Lithotripsy, Part IV, Chapter 38, pp. 317-332.
Concise Description of Relevance Accompanying Third Party Preissuance Submission Under 37 CFR 1.290 for U.S. Appl. No. 15/817,073, filed Aug. 5, 2019, 31 pages.
Concise Description of Relevance Accompanying Third Party Preissuance Submission Under 37 CFR 1.290 U.S. Appl. No. 16/240,556, filed Sep. 20, 2019, 14 pages.
Connors et al. (2003). "Renal Nerves Mediate Changes in Contralateral Renal Blood Flow after Extracorporeal Shockwave Lithotripsy," Nephron Physiology, vol. 95, pp. 67-75.
Deagon (2019). "Technology—Shockwave Medical IPO Soars On First Day Of Trading," Investor's Business Daily, Available Online at <https://www.investors.com/news/technology/shockwave-medical-ipo-soars-trading/>, pp. 1-15.
Decision Instituting Inter Partes Review of U.S. Pat. No. 9,642,673, by the Patent Trial and Appeal Board dated Jul. 22, 2019, 22 pages.
Decision to Grant received for European Patent Application No. 13756766.5, mailed on May 27, 2016, 2 pages.
Decision to Grant received for European Patent Application No. 13827971.6, mailed on Jan. 31, 2019, 2 pages.
Decision to Grant received for Japanese Patent Application No. 2011-513694, mailed on Oct. 7, 2014, 3 pages.

(56) References Cited

OTHER PUBLICATIONS

Declaration of Dr. Morten Olgaard Jensen, Dec. 6, 2018, pp. 1-113.
Declaration of Juanita DeLoach, Exhibit 1236, Case IPR2019-00408 Feb. 18, 2020, 4 pages.
Declaration of Natalie J. Grace, Apr. 22, 2019, pp. 1-5.
Declaration of William Patrick Stephens, Apr. 22, 2019, pp. 1-6.
Dodd (1842). "Two Cases of Calculus in the Bladder, in Which Lithotripsy Was Performed," Provincial Medical & Surgical Journal, 3(71):368-370.
Drilling Research on the Electrical Detonation and Subsequent Cavitation in a Liquid Technique (Spark Drilling), Drilling Research Division-5718, Sandia Laboratories, Status Report Jul. 1-Dec. 31, 1975, 53 pages.
Extended European Search Report (includes Supplementary European Search Report and Search Opinion) received for European Patent Application No. 09763640.1, mailed on Oct. 10, 2013, 5 pages.
Extended European Search Report received for European Patent Application No. 13827971.6, mailed on Apr. 12, 2016, 8 pages.
FDA Clears Lithoplasty Balloon That Shatters Calcified Lesions With Ultrasound, Diagnostic and Interventional Cardiology, Available Online at <https://www.dicardiology.com/product/fda-clearslithoplasty-balloon-shatters-calcified-lesions-ultrasound>, Sep. 16, 2016, pp. 1-5.
File History for U.S. Pat. No. 9,642,673, May 9, 2017, pp. 1-1789.
Final Office Action received for U.S. Appl. No. 12/482,995, mailed on Feb. 20, 2014, 11 pages.
Final Office Action received for U.S. Appl. No. 12/581,295, mailed on Jun. 5, 2014, 14 pages.
Final Office Action received for U.S. Appl. No. 13/049,199 mailed on Aug. 11, 2014, 8 pages.
Final Office Action received for U.S. Appl. No. 13/267,383, mailed on May 28, 2015, 12 pages.
Final Office Action received for U.S. Appl. No. 13/267,383, mailed on Oct. 25, 2013, 8 pages.
Final Office Action received for U.S. Appl. No. 13/534,658, mailed on Aug. 23, 2016, 11 pages.
Final Office Action received for U.S. Appl. No. 13/615,107, mailed on Sep. 1, 2015, 9 pages.
Final Office Action received for U.S. Appl. No. 13/646,570, mailed on Dec. 23, 2014, 10 pages.
Final Office Action received for U.S. Appl. No. 14/271,342, mailed on Feb. 27, 2015, 7 pages.
Final Office Action received for U.S. Appl. No. 15/346,132, mailed on Jun. 5, 2019, 12 pages.
Final Office Action received for U.S. Appl. No. 15/979,182, mailed on Oct. 21, 2019, 6 pages.
Fung (1993). "Biomechanics—Mechanical Properties of Living Tissues," Second Edition, Springer, 14 pages.
Gambihler et al. (1994). "Permeabilization of the Plasma Membrane of L1210 Mouse Leukemia Cells Using Lithotripter Shock Waves," The Journal of Membrane Biology, vol. 141, pp. 267-275.
Goryachev et al. "Mechanism of Electrode Erosion in Pulsed Discharges in Water with a Pulse Energy of ~1 J," Tech. Phys. Lett. vol. 23(5):386-387.
Gottlieb (2018). "U.S. Department of Health and Human Services, Food and Drug Administration Report to Congress by Scott Gottlieb," Exhibit 1217, 10 pages.
Grassi et al. (2012). "Novel Antihypertensive Therapies: Renal Sympathetic Nerve Ablation and Carotid Baroreceptor Stimulation," Current Hypertension Reports, vol. 14, pp. 567-572.
Grocela et al. (1997). "Intracorporeal Lithotripsy. Instrumentation and Development," Urologic Clinics of North America, 24(1):13-23.
Hawkins et al. U.S. Appl. No. 61/061,170, filed Jun. 13, 2008, titled "Shockwave Balloon Catheter System". pp. 1-50.
Hill (2019). "Deposition Transcript (compressed) of Jonathan M. Hill, M.d.," Exhibit 1211, Case No. IPR2019-00408, U.S. Pat. No. 9,642,673, 63 pages.

Intention to Grant received for European Patent Application No. 13756766.5, mailed on Jan. 8, 2016, 5 pages.
Intention to Grant received for European Patent Application No. 13827971.6, mailed on Sep. 28, 2018, 8 pages.
International Preliminary Report on Patentability received for PCT Patent Application No. PCT/US2009/047070, mailed on Dec. 23, 2010, 7 pages.
International Preliminary Report on Patentability received for PCT Patent Application No. PCT/US2011/047070, mailed on Feb. 21, 2013, 7 pages.
International Preliminary Report on Patentability received for PCT Patent Application No. PCT/US2012/023172, mailed on Aug. 15, 2013, 6 pages.
International Preliminary Report on Patentability received for PCT Patent Application No. PCT/US2012/063925, mailed on May 22, 2014, 12 pages.
International Preliminary Report on Patentability received for PCT Patent Application No. PCT/US2013/031805, mailed on Feb. 19, 2015, 11 pages.
International Preliminary Report on Patentability received for PCT Patent Application No. PCT/US2013/039987, issued on Nov. 20, 2014, 11 pages.
International Preliminary Report on Patentability received for PCT Patent Application No. PCT/US2013/048277, mailed on Jan. 8, 2015, 9 pages.
International Preliminary Report on Patentability received for PCT Patent Application No. PCT/US2013/055431, mailed on Feb. 26, 2015, 7 pages.
International Preliminary Report on Patentability received for PCT Patent Application No. PCT/US2013/059533, mailed on Mar. 26, 2015, 10 pages.
International Preliminary Report on Patentability received for PCT Patent Application No. PCT/US2016/060817, mailed on May 31, 2018, 9 pages.
International Preliminary Report on Patentability received for PCT Patent Application No. PCT/US2018/059083, mailed on May 28, 2020, 7 pages.
International Search Report and Written Opinion received for PCT Patent Application No. PCT/US2013/031805, mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
International Search Report and Written Opinion received for PCT Patent Application No. PCT/US2013/055431, mailed on Nov. 12, 2013, 9 pages.
International Search Report and Written Opinion received for PCT Patent Application No. PCT/US2013/059533, mailed on Nov. 7, 2013, 14 pages.
International Search Report and Written Opinion received for PCT Patent Application No. PCT/US2015/029088, mailed on Jul. 16, 2015, 13 pages.
International Search Report and Written Opinion received for PCT Patent Application No. PCT/US2016/060817, mailed on Feb. 20, 2017, 13 pages.
International Search Report received for PCT Patent Application No. PCT/US2009/047070, mailed on Jan. 19, 2010, 4 pages.
International Search Report received for PCT Patent Application No. PCT/US2012/023172, mailed on Sep. 28, 2012, 3 pages.
International Written Opinion received for PCT Patent Application No. PCT/US2009/047070, mailed on Jan. 19, 2010, 5 pages.
International Written Opinion received for PCT Patent Application No. PCT/US2011/047070, mailed on May 1, 2012, 5 pages.
International Written Opinion received for PCT Patent Application No. PCT/US2012/023172, mailed on Sep. 28, 2012, 4 pages.
International Search Report and Written Opinion Received for PCT Application No. PCT/US2018/059083, mailed on Jan. 22, 2019, 8 pages.

(56) References Cited

OTHER PUBLICATIONS

International Search Report and Written Opinion received for PCT Patent Application No. PCT/US2020/046134, mailed on Oct. 26, 2020, 18 pages.
Jacob (1993). "Applications and Design with Analog Integrated Circuits," Second Edition, Prentice-Hall International Editions, pp. 1-8.
Jahnke et al. (2008). "Retrospective Study of Rapid-Exchange Monorail Versus Over-the-Wire Technique for Femoropopliteal Angioplasty," Cardiovascular and Interventional Radiology, vol. 31, pp. 854-859.
Jensen, Morten O. "Supplemental Declaration of Dr. Morten Olgaard Jensen in Support of Petitioner's Reply," Case IPR2019-00408, U.S. Pat. No. 9,642,673 B2, Feb. 18, 2020, 54 pages.
Johnson et al. (1992). "Electric Circuit Analysis—Second Edition," Prentice-Hall International Editions, pp. 1-17.
Kaplan et al. (1993). "Healing after Arterial Dilatation with Radiofrequency Thermal and Nonthermal Balloon Angioplasty Systems," Journal of Investigative Surgery, vol. 6, pp. 33-52.
Kereiakes, Dean J. "Deposition Transcript (compressed) of Dean J. Kereiakes", Exhibit 1213, Cases No. 2019-00405, 00408 and 00409, Jan. 7, 2020., 65 pages.
Kodama et al. (2002). "Shock Wave-Mediated Molecular Delivery into Cells," Biochimica et Biophysica Acta. vol. 1542, pp. 186-194.
Laeseke et al. (2006). "Multiple-Electrode RF Ablation Creates Confluent Areas of Necrosis: Results in in vivo Porcine Liver," Radiology, 241(1):116-124.
Lauer et al. (1997). "Shock Wave Permeabilization as a New Gene Transfer Method," Gene Therapy, vol. 4, pp. 710-715.
Linnemeier et al. (1993). "Radiation Exposure: Comparison of Rapid Exchange and Conventional Over-the-Wire Coronary Angioplasty Systems," Catheterization and Cardiovascular Diagnosis, vol. 30, pp. 11-14.
Liu et al. (2015). "Current Understanding of Coronary Artery Calcification," Journal of Geriatric Cardiology, vol. 12, pp. 668-675.
Llewellyn-Jones (1963). "The Mechanism of Electrode Erosion in Electrical Discharges," Platinum Metals Rev. vol. 7(2):58-65.
Loske (2007). "Shock Wave Physics for Urologists," Universidad Nacional Autónoma de México, pp. 1-188.
Millman et al. (1987). "Microelectronics—Second Edition," McGraw-Hill International Editions, pp. 1-15.
Mills et al. (2019). "Cracking the Code on Calcium; Initiate with BUY, $39 Target," Canaccord Genuity—Capital Markets, US Equity Research, pp. 1-63.
Mitomo (2018). "Intravascular lithotripsy: A Novel Technology for Treating Calcified Coronary Stenoses," Cardiovascular News, Online Available at <https://cardiovascularnews.com/intravascular-lithotripsy-anovel-technology-for-treating-calcified-coronary-stenoses>, pp. 1-4.
Mooney et al. (1990). "Monorail Piccolino Catheter: A New Rapid Exchange/Ultralow Profile Coronary Angioplasty System," Catheterization and Cardiovascular Diagnosis, vol. 20, pp. 114-119.
Nichols et al. (2005). "McDonald's Blood Flow in Arteries: Theoretical, Experimental and Clinical Principles," 5th Edition, Oxford University Press, pp. 1-9.
Nisonson et al. (1986). "Ambulatory Extracorporeal Shockwave Lithotripsy," Urology, 28(5):381-384.
Non Final Office Action received for U.S. Appl. No. 12/611,997, mailed on Nov. 26, 2014, 8 pages.
Non-Final Office Action received for U.S. Appl. No. 12/482,995, mailed on Aug. 13, 2014, 10 pages.
Non-Final Office Action received for U.S. Appl. No. 12/482,995, mailed on Jul. 12, 2013, 11 pages.
Non-Final Office Action received for U.S. Appl. No. 12/501,619, mailed on Jan. 28, 2014, 10 pages.
Non-Final Office Action received for U.S. Appl. No. 12/581,295, mailed on Jan. 15, 2015, 14 pages.
Non-Final Office Action received for U.S. Appl. No. 12/581,295, mailed on Mar. 10, 2014, 11 pages.
Non-Final Office Action received for U.S. Appl. No. 13/049,199, mailed on Feb. 4, 2014, 8 pages.
Non-Final Office Action received for U.S. Appl. No. 13/267,383, mailed on Feb. 25, 2015, 9 pages.
Non-Final Office Action received for U.S. Appl. No. 13/465,264, mailed on Dec. 23, 2014, 13 pages.
Non-Final Office Action received for U.S. Appl. No. 13/465,264, mailed on Oct. 29, 2014, 13 pages.
Non-Final Office Action received for U.S. Appl. No. 13/534,658, mailed on Mar. 11, 2016, 12 pages.
Non-Final Office Action received for U.S. Appl. No. 13/615,107, mailed on Apr. 24, 2015, 9 pages.
Non-Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Non-Final Office Action received for U.S. Appl. No. 14/061,554, mailed on Mar. 12, 2014, 14 pages.
Non-Final Office Action received for U.S. Appl. No. 14/079,463, mailed on Mar. 4, 2014, 9 pages.
Non-Final Office Action received for U.S. Appl. No. 14/271,276, mailed on Aug. 4, 2014, 7 pages.
Non-Final Office Action received for U.S. Appl. No. 14/271,342, mailed on Sep. 2, 2014, 6 pages.
Non-Final Office Action received for U.S. Appl. No. 14/273,063, mailed on Jun. 3, 2016, 9 pages.
Non-Final Office Action received for U.S. Appl. No. 14/515,130, mailed on Jan. 14, 2016, 16 pages.
Non-Final Office Action received for U.S. Appl. No. 15/346,132, mailed on Dec. 20, 2018, 14 pages.
Non-Final Office Action received for U.S. Appl. No. 15/474,885, mailed on Oct. 5, 2017, 9 pages.
Non-Final Office Action received for U.S. Appl. No. 15/817,073, mailed on Nov. 12, 2019, 18 pages.
Non-Final Office Action received for U.S. Appl. No. 15/979,182, mailed on Aug. 9, 2019, 6 pages.
Non-Final Office Action received for U.S. Appl. No. 16/893,400, mailed on Aug. 1, 2022, 9 pages.
Notice of Acceptance received for Australian Patent Application No. 2009257368, mailed on Aug. 28, 2014, 2 pages.
Notice of Acceptance received for Australian Patent Application No. 2013284490, mailed on May 8, 2018, 3 pages.
Notice of Acceptance received for Australian Patent Application No. 2013300176, mailed on Aug. 7, 2017, 3 pages.
Notice of Acceptance received for Australian Patent Application No. 2018204691, mailed on Jun. 18, 2019, 3 pages.
Notice of Allowance received for Canadian Patent Application No. 2,727,429, mailed on May 26, 2015, 1 page.
Notice of Allowance received for Canadian Patent Application No. 2,881,208, mailed on Oct. 24, 2019, 1 page.
Notice of Allowance received for Chinese Patent Application No. 201380041656.1, mailed on Mar. 3, 2017, 4 pages.
Notice of Allowance received for European Patent Application No. 18804877.1, mailed on May 24, 2022, 5 pages.
Notice of Allowance received for Japanese Patent Application No. 2015-520522, mailed on Feb. 23, 2017, 3 pages.
Notice of Allowance received for Japanese Patent Application No. 2015-526523, mailed on Dec. 4, 2017, 3 pages (Official Copy Only) (See Communication under 37 CFR § 1.98(a) (3)).
Notice of Allowance received for U.S. Appl. No. 12/482,995, mailed on Dec. 24, 2014, 6 pages.
Notice of Allowance received for U.S. Appl. No. 12/581,295, mailed on Jul. 10, 2015, 15 pages.
Notice of Allowance received for U.S. Appl. No. 12/581,295, mailed on Jul. 29, 2015, 7 pages.
Notice of Allowance received for U.S. Appl. No. 13/049,199, mailed on Dec. 15, 2014, 7 pages.
Notice of Allowance received for U.S. Appl. No. 13/049,199, mailed on Jan. 13, 2015, 4 pages.
Notice of Allowance received for U.S. Appl. No. 13/465,264, mailed on May 8, 2015, 7 pages.
Notice of Allowance received for U.S. Appl. No. 13/534,658, mailed on Jan. 5, 2017, 6 pages.

(56) References Cited

OTHER PUBLICATIONS

Notice of Allowance received for U.S. Appl. No. 13/534,658, mailed on Jan. 18, 2017, 4 pages.
Notice of Allowance received for U.S. Appl. No. 13/646,570, mailed on Mar. 11, 2015, 7 pages.
Notice of Allowance received for U.S. Appl. No. 13/777,807, mailed on May 19, 2015, 13 pages.
Notice of Allowance received for U.S. Appl. No. 13/831,543, mailed on Oct. 8, 2014, 14 pages.
Notice of Allowance received for U.S. Appl. No. 14/061,554, mailed on Apr. 25, 2014, 8 pages.
Notice of Allowance received for U.S. Appl. No. 14/079,463, mailed on Apr. 1, 2014, 5 pages.
Notice of Allowance received for U.S. Appl. No. 14/218,858, mailed on Aug. 26, 2016, 8 pages.
Notice of Allowance received for U.S. Appl. No. 14/271,276, mailed on Feb. 25, 2015, 8 pages.
Notice of Allowance received for U.S. Appl. No. 14/271,342, mailed on Mar. 13, 2015, 5 pages.
Notice of Allowance received for U.S. Appl. No. 14/515,130, mailed on May 2, 2016, 8 pages.
Notice of Allowance received for U.S. Appl. No. 14/515,130, mailed on May 25, 2016, 3 pages.
Notice of Allowance received for U.S. Appl. No. 15/220,999, mailed on Oct. 10, 2018, 10 pages.
Notice of Allowance received for U.S. Appl. No. 15/346,132, mailed on Aug. 21, 2019, 8 pages.
Notice of Allowance received for U.S. Appl. No. 15/346,132, mailed on Dec. 17, 2019, 7 pages.
Notice of Allowance received for U.S. Appl. No. 15/474,885, mailed on Feb. 14, 2018, 5 pages.
Notice of Allowance received for U.S. Appl. No. 15/817,073, mailed on Mar. 13, 2020, 8 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Office Action received for Australian Patent Application No. 2013284490, mailed on Jun. 5, 2017, 4 pages.
Office Action received for Australian Patent Application No. 2013284490, mailed on May 3, 2018, 5 pages.
Office Action received for Australian Patent Application No. 2013300176, mailed on Nov. 10, 2016, 2 pages.
Office Action received for Australian Patent Application No. 2018204691, mailed on Jul. 12, 2018, 2 pages.
Office Action received for Canadian Patent Application No. 2,727,429, mailed on Apr. 14, 2015, 4 pages.
Office Action received for Canadian Patent Application No. 2,877,160, mailed on Feb. 7, 2019, 4 pages.
Office Action received for Canadian Patent Application No. 2,881,208, mailed on Feb. 12, 2019, 4 pages.
Office Action received for Chinese Patent Application No. 201380033808.3, mailed on Jul. 5, 2016, 9 pages.
Office Action received for Chinese Patent Application No. 201380041656.1, mailed on Jul. 5, 2016, 9 pages.
Office Action received for Chinese Patent Application No. 201380042887.4, mailed on Aug. 8, 2016, 9 pages.
Office Action received for European Patent Application No. 13735174.8, mailed on Oct. 15, 2018, 5 pages.
Office Action received for Japanese Patent Application No. 2011-513694, mailed on Aug. 27, 2013, 6 pages.
Office Action received for Japanese Patent Application No. 2011-513694, mailed on Jun. 10, 2014, 4 pages.
Office Action received for Japanese Patent Application No. 2011-534914, mailed on Jul. 15, 2014, 3 pages.
Office Action received for Japanese Patent Application No. 2014-158517, mailed on May 19, 2015, 5 pages.
Office Action received for Japanese Patent Application No. 2015-526523, mailed on Jan. 25, 2017, 8 pages.

Patent Owner Preliminary Response for U.S. Pat. No. 9,642,673, by the Patent Trial and Appeal Board dated Apr. 24, 2019, 56 pages.
Patterson et al. (1985). "The Etiology and Treatment of delayed Bleeding following Percutaneous Lithotripsy," The Journal of Urology, vol. 133, pp. 447-451.
Petition for Inter Partes Review of U.S. Pat. No. 9,642,673, issued on May 9, 2017, 77 pages.
Petitioner Power of Attorney for U.S. Pat. No. 9,642,673, dated Dec. 6, 2018, pp. 1-2.
Petitioner's Reply Brief, Dated Feb. 18, 2020, 32 pages.
Publicly Available Professional & Educational Background Summary for Actus Medical, Nov. 2, 2020, 9 pages.
Publicly Available Professional & Educational Background Summary for Alex Asconeguy, Nov. 2, 2020, 4 pages.
Publicly Available Professional & Educational Background Summary for Chris Kunis, 2012, 3 pages.
Publicly Available Professional & Educational Background Summary for Clifton Alferness, 2013, 3 pages.
Publicly Available Professional & Educational Background Summary for Daniel Hawkins, 2018, 2 pages.
Publicly Available Professional & Educational Background Summary for Doug Hakala, 2016, 5 pages.
Publicly Available Professional & Educational Background Summary for J. Christopher Flaherty, Nov. 2, 2020, 2 pages.
Publicly Available Professional & Educational Background Summary for John Adams, 2009, 2 pages.
Publicly Available Professional & Educational Background Summary for Michael D. Lesh, 2017, 4 pages.
Publicly Available Professional & Educational Background Summary for Randy Werneth, Nov. 2, 2020, 3 pages.
Publicly Available Professional & Educational Background Summary for Tom Goff, 2017, 3 pages.
Ricks (2019). "Long Island Doctors Using Sound Waves to Loosen Calcium Deposits from Arteries, Restore Blood Flow," News/Health, Available Online at <https://www.newsday.com/news/health/calcium-treatment-st-francis-hospital-1.27314331>, pp. 1-4.
Rocha-Singh et al. (2014). "Peripheral Arterial Calcification: Prevalence, Mechanism, Detection, and Clinical Implications," Catheterization and Cardiovascular Interventions, vol. 86, pp. E212-E220.
Rosenschein et al. (1992). "Shock-Wave Thrombus Ablation, a New Method for Noninvasive Mechanical Thrombolysis," The American Journal of Cardiology, vol. 70, pp. 1358-1361.
shockwavemedical.com, "Intravascular Lithotripsy (IVL)," Available Online at <https://shockwavemedical.com/technology/intravascular-lithotripsy-ivl/?country=Egypt>, 2019, pp. 1-4.
Simpson et al. (1962). "A New Catheter System for Coronary Angioplasty," The American Journal of Cardiology, vol. 49, pp. 1216-1222.
Soukas, Peter, "Deposition Transcript (compressed) of Peter Soukas," Cases: IPR2019-00405, IPR2019-00408, IPR2019-00409, Dec. 30, 2019, 81 pages.
Stephens, William, "Deposition Transcript (compressed) of William Patrick Stephens," Case No. IPR2019-00408, Jan. 22, 2020, 55 pages.
Summons to attend oral proceedings received for European Patent Application No. 18804877.1 mailed on Dec. 23, 2021, 7 pages.
Sweers et al. (2012). "Lightning Strikes: Protection, Inspection, and Repair," Aero Magazine, Quarter 4, pp. 19-28.
Tanaka et al. (2001). "A New Radiofrequency Thermal Balloon Catheter for Pulmonary Vein Isolation," Journal of the American College of Cardiology, 38(7):2079-2086.
Third Party Preissuance Submission for U.S. Appl. No. 16/240,556, filed Sep. 20, 2019, 3 pages.
Third-Party Submission Under 37 CFR 1.290 Concise Description of Relevance for U.S. Appl. No. 16/240,556, filed Sep. 20, 2019, 4 pages.
Third Party Preissuance Submission for U.S. Appl. No. 15/817,073, filed Aug. 5, 2019, 3 pages.
Third-Party Submission Under 37 CFR 1.290 Concise Description of Relevance for U.S. Appl. No. 15/817,073, filed Aug. 5, 2019, 3 pages.
Tomlinson (1991). "Electrical Networks and Filters: Theory and Design," Prentice Hall, pp. 1-9.

(56) References Cited

OTHER PUBLICATIONS

Top Cardiovascular Innovation Award, Cardiovascular Research Technologies (CRT), 2015, p. 1.
Viljoen (2008). "Flashover Performance of a Rod-Rod Gap Containing a Floating Rod Under Switching Impulses with Critical and Near Critical Times to Crest," A Dissertation Submitted to the Faculty of Engineering and the Built Environment, University of the Witwatersrand, 128 pages.
Vorreuther et al. (1992). "Impact of Voltage and Capacity on the Electrical and Acoustic Output of Intracorporeal Electrohydraulic Lithotripsy," Urological Research, 20(5):355-359.
Vorreuther et al. (1992). "Publication Information—Impact of Voltage and Capacity on the Electrical and Acoustic Output of Intracorporeal Electrohydraulic Lithotripsy," Urological Research, 20, No. 5, Available Online at <https://rd.springer.com/article/10.1007/BF00922748>): pp. 1-3.
Wagner et al. (1961). "Mechanism of Breakdown of Laboratory Gaps," Transactions of the American Institute of Electrical Engineers. Part III: Power Apparatus and Systems, 80(3):604-618.
Wakerly (1990). "Digital Design: Principles and Practices," Prentice Hall Inc., pp. 1-19.
Weide, Daniel, "Deposition Transcript (compressed) of Daniel Van Der Weide, Ph.d.," Exhibit 1203, Case No. IPR2019-00408, U.S. Pat. No. 9,642,673 B2, Jan. 13, 2020, 94 pages.
Weide, Daniel, "Exhibit 1116 to Deposition of Daniel Van Der Weide," Jan. 13, 2020, 1 page.
Weide, Daniel, "Exhibit to 1117 Deposition of Daniel Van Der Weide, Ph.d.," Jan. 13, 2020, 1 page.
Weide, Daniel, "Exhibit to 1118 Deposition of Daniel Van Der Weide, Ph.d.," Jan. 13, 2020, 1 page.
Wells Fargo Securities LLC, "SWAV: Initiating With A Market Perform Rating," Shockwave Medical Inc., Apr. 1, 2019, pp. 1-34.
Whitaker (2001). "Modelling of Three-Dimensional Field Around Lightning Rods," University of Tasmania, pp. 1-64.
Whitaker (2001). "Publication Information—Modelling of Three-Dimensional Field Around Lightning Rods," University of Tasmania, 1 page.
Final Written Decision for IPR2019-00408 dated Jul. 20, 2020, 62 pages.
Opening Brief of Appellant Shockwave Medical, Inc. for Case No. 20-2314 dated Feb. 3, 2021, 158 pages.
Brief for Appellee Cardiovascular Systems, Inc. for CAFC Case No. 20-2314 dated Apr. 14, 2021, 71 pages.
Zhong et al. (1997). "Transient Oscillation of Cavitation Bubbles Near Stone Surface During Electrohydraulic Lithotripsy," Journal of Endourology, 11(1):55-61.

* cited by examiner

| Sample 1 | |
|---|---|
| Trial | Sonic Output (mV) |
| 1 | 424 |
| 2 | 440 |
| 3 | 408 |
| 4 | 600 |
| 5 | 408 |
| 6 | 432 |
| 7 | 536 |
| 8 | 600 |
| 9 | 368 |
| 10 | 488 |
| 11 | 440 |
| 12 | 608 |
| 13 | 488 |
| 14 | 472 |
| 15 | 616 |
| 16 | 488 |
| 17 | 440 |
| 18 | 424 |
| 19 | 472 |
| 20 | 440 |
| Average | 479.6 |

FIG. 4A

| Sample 2 | |
|---|---|
| Trial | Sonic Output (mV) |
| 1 | 600 |
| 2 | 440 |
| 3 | 448 |
| 4 | 440 |
| 5 | 616 |
| 6 | 600 |
| 7 | 360 |
| 8 | 376 |
| 9 | 624 |
| 10 | 480 |
| 11 | 360 |
| 12 | 440 |
| 13 | 352 |
| 14 | 368 |
| 15 | 392 |
| 16 | 408 |
| 17 | 392 |
| 18 | 368 |
| 19 | 432 |
| 20 | 480 |
| Average | 448.8 |

FIG. 4B

SHOCK WAVE ELECTRODES

CROSS-REFERENCE TO RELATED APPLICATIONS

This application is a divisional of U.S. patent application Ser. No. 17/725,435, filed Apr. 20, 2022, which in turn is a divisional of U.S. patent application Ser. No. 16/691,449, filed Nov. 21, 2019, now U.S. Pat. No. 11,337,713, which in turn a divisional of U.S. patent application Ser. No. 15/346,132 filed Nov. 8, 2016, now U.S. Pat. No. 10,555,744, which claims priority to U.S. Provisional Patent Application Ser. No. 62/257,141, filed on Nov. 18, 2015, all of which are hereby incorporated by reference in their entirety for all purposes.

FIELD

The present disclosure relates generally to shock wave electrodes, and, more specifically, to electrodes for the generation of shock waves within vascular structures.

BACKGROUND

Electrohydraulic lithotripsy has been typically used for breaking calcified deposits or "stones" in the urinary or biliary track. Recent work by the assignee shows that lithotripsy electrodes may similarly be useful for breaking calcified plaques in the wall of a vascular structure. Shock waves generated by lithotripsy electrodes may be used to controllably fracture a calcified lesion to help prevent sudden stress and injury to the vessel or valve wall when it is dilated using a balloon. A method and system for treating stenotic or calcified vessels is described in U.S. Pat. Nos. 8,956,371, 8,888,788, and 9,011,463 incorporated herein by reference. A method and system for treating stenotic or calcified aortic valves is described in U.S. Pat. No. 9,044,618 incorporated herein by reference. As described in those applications, a balloon is placed adjacent leaflets of a valve or vessel to be treated and is inflated with a liquid. Within the balloon are one or more shock wave electrodes that produce shock waves that propagate through the liquid and impinge upon the valve or vessel. The impinging shock waves soften, break and/or loosen the calcified regions for removal or displacement to open the valve or vessel (e.g., to enlarge the valve opening or clear the lumen of the vessel).

In electrode-based lithotripsy systems, a pair of electrodes is used to generate a shock wave. When a high voltage is applied across the electrode pair, a plasma arc forms between them, giving rise to a steam bubble in the fluid. A first shock wave occurs when the steam bubble first forms and a second shock wave occurs as the steam bubble collapses. The timing and size of the bubble, along with the sonic output and propagation direction of the resultant shock waves, depend at least in part on the location, geometry and size of the electrodes. The size and arrangement of the electrodes also impact the types of vascular structures that may be accessed and treated by the shock wave catheter. For example, coaxial shock wave electrode pairs can comprise an inner wire that is inserted within an outer cable, where the conductive portions of each are exposed at the tips. In this arrangement, a high voltage applied across the inner wire and outer cable gives rise to a shock wave that propagates away from the exposed tips of the inner wire and outer cable. Additional improved lithotripsy or shock wave electrodes that can readily access and generate sufficient sonic output to treat various locations in the vasculature for angioplasty and/or valvuloplasty procedures may be desirable.

BRIEF SUMMARY

Described herein are electrodes for the generation of shock waves within vascular structures. One variation of a shock wave electrode pair comprises a first electrode that is circumferentially disposed over an outer surface of an elongate member and a second electrode also circumferentially disposed over the outer surface of the elongate member, where a spark gap is formed at the narrowest separation distance between the two electrodes. The first and second electrodes may be coplanar along the surface of the elongate member (e.g., located along a single layer). In some variations, the first electrode may comprise a recess and the second electrode may comprise a projection that is located within the recess such that the separation between the projection and the recess form the spark gap. Each electrode may comprise a portion that is covered by an insulating layer or coating and a portion that is not covered by an insulating layer or coating so that the electrically conductive substrate of the electrode is exposed. A catheter may have one or more of these electrode pairs arranged in series. In use, a voltage generator may be provided and a first wire may connect the proximal-most electrode to a positive terminal of the voltage generator and a second wire may connect the distal-most electrode to a negative terminal of the voltage generator, and a high voltage may be applied across the positive and negative terminals in order to generate a series of shock waves along the length of the catheter at each of the electrode pairs.

One variation of a shock wave catheter may comprise an axially extending elongate member, a first electrode circumferentially disposed over an outer surface of the elongate member, the first electrode comprising a recess along an edge of the first electrode, and a second electrode circumferentially disposed over the outer surface of the elongate member and adjacent to the first electrode, the second electrode comprising a projection along the edge of the second electrode that is received by the recess. A spark gap may be formed by a separation between the projection and the recess. The catheter may be configured such that when a voltage is applied across the first and second electrodes, a current may flow across the spark gap between the first electrode and the second electrode such that a shockwave is initiated at the spark gap. Some systems may further comprise a voltage source and a first wire that connects the first electrode to a positive terminal of the voltage source, and a second wire connects the second electrode to a negative terminal of the voltage source. The first wire and the second wire may be located on the outer surface of the elongate member. The axially extending elongate member may comprise a guide wire lumen extending therethrough. Some shock wave catheter variations may further comprise a third electrode circumferentially disposed over the outer surface of the elongate member and adjacent to the second electrode, where the second electrode may comprise a recess and the third electrode may comprise a projection that is received by the recess of the second electrode, and where a space between the projection of the third electrode and the recess of the second electrode may form a second spark gap such that when a voltage is applied across the first and third electrodes, a current may flow across the first spark gap to initiate a first shock wave and across the second spark gap to initiate a second shock wave.

In some variations, the shock wave catheter may further comprise a fourth electrode circumferentially disposed over the outer surface of the elongate member and adjacent to the third electrode, and a fifth electrode circumferentially disposed over the outer surface of the elongate member and adjacent to the fourth electrode. The fourth electrode may comprise a projection that is received by a recess of the third electrode, and a space between the projection of the fourth electrode and the recess of the third electrode may form a third spark gap. The fourth electrode may also comprise a recess that receives a projection of the fifth electrode, and a space between the recess of the fourth electrode and the protrusion of the fifth electrode may form a fourth spark gap so that when a voltage is applied across the first and fifth electrodes, a current may flow across the first spark gap to initiate a first shock wave, across the second spark gap to initiate a second shock wave, across the third spark gap to initiate a third shock wave, and across the fourth spark gap to initiate a fourth shock wave. Optionally, some shock wave catheters may further comprise a sixth electrode circumferentially disposed over the outer surface of the elongate member and adjacent to the fifth electrode, and a seventh electrode circumferentially disposed over the outer surface of the elongate member and adjacent to the sixth electrode. The sixth electrode may comprise a projection that is received by a recess of the fifth electrode, and a space between the projection of the sixth electrode and the recess of the fifth electrode may form a fifth spark gap. The sixth electrode may further comprise a recess that receives a projection of the seventh electrode, and a space between the recess of the sixth electrode and the protrusion of the seventh electrode may form a sixth spark gap such that when a voltage is applied across the first and seventh electrodes, a current may flow across the first spark gap to initiate a first shock wave, across the second spark gap to initiate a second shock wave, across the third spark gap to initiate a third shock wave, across the fourth spark gap to initiate a second shock wave, across the fifth spark gap to initiate a fifth shock wave, and across the sixth spark gap to initiate a sixth shock wave.

Any of the electrode pairs described herein may comprise a first electrode having a recess and a second electrode adjacent to and co-planar with the first electrode and having a protrusion and the recess may have a concave curve and the protrusion may have a convex curve that corresponds with the concave curve. An electrode may comprise a proximal end, a distal end, and a spiral body therebetween. The spiral body may comprise one or more helices that wrap along the outer surface of the elongate body.

Another variation of a shock wave catheter may comprise an axially extending elongate member, a first electrode circumferentially disposed over an outer surface of the elongate member, the first electrode comprising a first electrically conductive region having a first surface area and a second electrode circumferentially disposed over the outer surface of the elongate member that is coplanar and adjacent to the first electrode. The second electrode may comprise a second electrically conductive region having a second surface area that is greater than the first surface area. A spark gap may be formed by a separation between the conductive region of the first electrode and the conductive region of the second electrode such that when a voltage is applied across the first and second electrodes, a current may flow across the spark gap between the first electrode and the second electrode such that a shockwave is initiated at the spark gap. Some variations may further comprise a voltage source, and a first wire may connect the first electrode to a positive terminal of the voltage source, and a second wire may connect the second electrode to a negative terminal of the voltage source, and the first wire and the second wire may be located on the outer surface of the elongate member. The axially extending elongate member may comprise a guide wire lumen extending therethrough. In some variations, the conductive region of the first electrode may have a first arcuate portion and the conductive region of the second electrode may have a second arcuate portion that is complementary to the first arcuate portion. For example, the first arcuate portion may comprise a convex curve and the second arcuate portion may comprise a concave curve. Alternatively or additionally, the first arcuate portion may comprise a concave curve and the second arcuate portion may comprise a convex curve. The radius of curvature of the first arcuate portion may be larger than the radius of curvature of the second arcuate portion, or alternatively, the radius of curvature of the first arcuate portion may be less than the radius of curvature of the second arcuate portion. The first arcuate portion may comprise a circular protrusion and the second arcuate portion may comprise a circular groove. Alternatively, the first arcuate portion may comprise a circular groove and the second arcuate portion may comprise a circular protrusion. A ratio of the surface area of the first conductive region to the surface area of the second conductive region may be from about 1:2 to about 1:20, e.g., from about 1:4 to about 1:10. The second electrode may comprise a proximal end, a distal end, and an electrically conductive body extending therebetween. The electrically conductive body may comprise one or more flexible spirals and/or one or more flexible helices. The electrically conductive body may comprise a flexible twisted portion.

Other variations of a shock wave catheter may comprise an axially extending elongate member, a first ring electrode mounted circumferentially around the elongate member, a second ring electrode mounted circumferentially around the elongate member and positioned adjacent to the first ring electrode, and a third ring electrode mounted circumferentially around the elongate member and positioned adjacent to the first ring electrode. A first spark gap may be defined between the first and second ring electrodes and a second spark gap may be defined between the second and third ring electrodes. Each spark gap may include an arcuate recess formed along a side edge of one of the ring electrodes and a complimentary arcuate projection formed along the side edge of the adjacent ring electrode, where the projection may fit into the associated recess. The first spark gap may be circumferentially offset from the second spark gap. The first and third ring electrodes may be connectable to a high voltage source. The second ring electrode may be a non-insulated metal and the recess of the first and second spark gaps may be formed in the second ring electrode. The projection of the first spark gap may be formed in the first ring electrode and the projection of the second spark gap may be formed in the third ring electrode, where the first and second ring electrodes may have an insulating coating except in the region of the projections. The surface area of the second ring electrode may be greater than the surface area of each of the projections of the first and third ring electrodes. The first electrode and the third electrode may each have a proximal portion, a distal portion, and a body therebetween, where the body may extend longitudinally along the axially extending elongate member and may comprise a spiral. In some variations, the body may comprise a helix, and/or one or more turns around the surface of the elongate member.

BRIEF DESCRIPTION OF THE DRAWINGS

FIG. 4A is a table that depicts experimental data that reflects the sonic output of a shock wave catheter similar to the shock wave catheter depicted in FIGS. 3A-3C, where the width of the spark gap is 0.003 inch. FIG. 4B is a table that depicts experimental data that reflects the sonic output of a shock wave catheter similar to the shock wave catheter depicted in FIGS. 3A-3C, where the width of the spark gap is 0.004 inch.

DETAILED DESCRIPTION

Figure 1A:
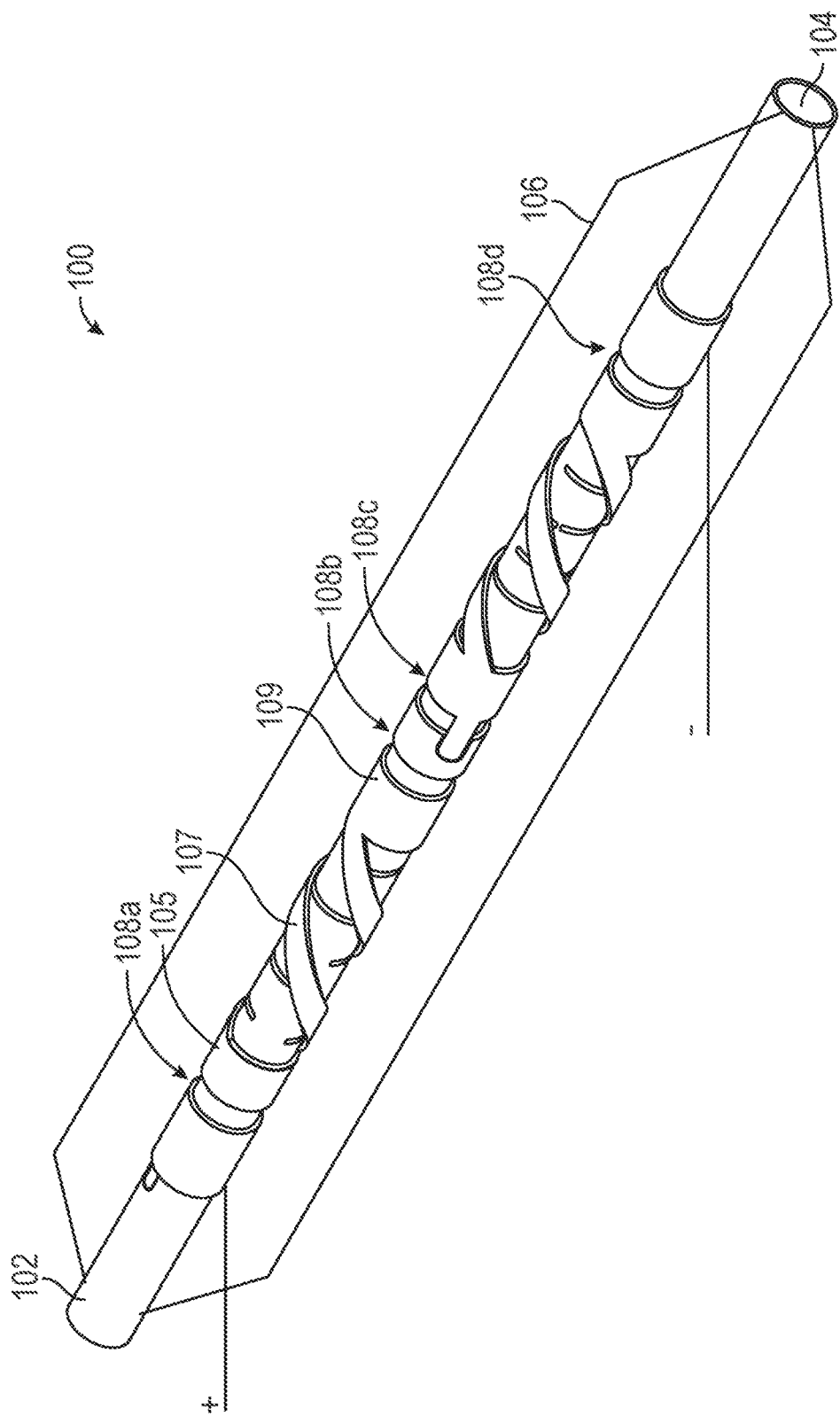
FIG. 1A depicts one variation of shock wave catheter comprising single-layer electrodes.

Described herein are electrodes for the generation of shock waves within vascular structures. One variation of a shock wave electrode pair comprises a first electrode that is circumferentially disposed over an outer surface of an elongate member and a second electrode also circumferentially disposed over the outer surface of the elongate member, where a spark gap may be formed at the narrowest separation distance between the two electrodes. The electrodes may be planar electrodes that are coplanar with each other (e.g., located along a single layer) over the outer surface of the elongate member (e.g., catheter). In some variations, the first electrode may have a recess (or protrusion) that corresponds with a protrusion (or groove) of the second electrode. The separation between the edge of the recess (or protrusion) of the first electrode and the edge of the protrusion (or recess) of the second electrode may be the shortest distance between the first and second electrodes, and form the spark gap. Multiple pairs of these coplanar or single-layer electrodes may be arranged in series along the surface of an elongate member. In a shock wave catheter system, a voltage generator comprising a positive terminal and a negative terminal may be provided, and a first wire may connect the proximal-most electrode with the positive terminal and a second wire may connect the distal-most electrode with the negative terminal, without the need for additional interconnecting wires between the electrode pairs. Reducing the number of wires that extend along the length of the elongate member may help to maintain the flexibility and steerability of the overall shock wave catheter system, which may facilitate the navigation of the shock wave catheter within tortuous vascular pathways. Reducing the number of wires along the length of the elongate member may also help reduce the thickness or diameter of the overall shock wave catheter. More generally, shock wave catheter systems comprising the single-layer electrodes described herein (i.e., where the surfaces of the first and second electrodes are coplanar) may have a reduced thickness or diameter as compared to shock wave catheter systems comprising stacked multi-layer electrodes (e.g., where the first electrode is on a first layer, the second electrode is on a second layer that is stacked over the first layer and an insulating layer that separates the first and second electrodes). For example, the diameter or thickness of an elongate member with single-layer electrodes may be about 0.025 inch or less, while the diameter or thickness of an elongate member with multi-layer electrodes may be about 0.032 inch or less. Some shock wave catheter systems comprise an angioplasty balloon having an inflated diameter of about 2 mm or less, and single-layer shock wave electrodes may be better suited for this size scale than multi-layer electrodes. In multi-layer electrode designs, shock waves are initiated by plasma arcs that extend across the insulating layer between the electrodes. However, for single-layer electrodes, the plasma arc extends across the spark gap between the electrodes along the surface of the elongate member, thereby eliminating the need for an additional insulating layer. Reducing the overall thickness of the electrode assembly and/or diameter of the shock wave catheter may allow the catheter to be navigated to smaller vascular structures for treatment. For example, shock wave catheters having single-layer electrodes may be more readily inserted in the coronary arteries than shock wave catheters having multi-layer electrodes.

FIG. 1A depicts an example of a shock wave catheter that may be advanced into a patient's vasculature. A shock wave catheter 100 may comprise an elongate member 102, a guide wire lumen 104, a tube 106, and one or more pairs of electrodes 108 enclosed within the tube 106. For procedures in vessels, the tube can be the form of an inflatable, angioplasty balloon. For valvuloplasty application, balloon may not be required. In some variations, a single electrode may be part of two electrode pairs. For example, the proximal end 105 of electrode 107 is part of electrode pair 108a and the distal end 109 of electrode 107 is part of electrode pair 108b. The balloon 106 may be collapsed while the shock wave catheter 100 navigates through the vasculature, and expanded (as shown in FIG. 1A) after the catheter is located at the desired treatment position. The catheter may comprise a fluid lumen (not shown) that is in communication with a fluid source that introduces fluid into the balloon 106. The shock wave catheter system may also comprise a voltage generator having a positive terminal and a negative terminal, and a first wire that connects that proximal-most electrode to the positive terminal and a second wire that connects the distal-most electrode to the negative terminal (of course, the polarity may be reversed). After the balloon has been expanded with a fluid to a certain pressure, a voltage pulse may be applied to the electrodes, thereby generating one or more shock waves that may propagate through the fluid and the balloon wall to impinge on a calcification in contact with the balloon. Shock waves may be generated repeatedly, as may be desirable by the practitioner. Although the shock wave catheter 100 is depicted as having four electrode pairs (e.g., electrode pairs 108a-d), it should be understood that other variations of shock wave catheters may have a different number of electrode pairs (e.g., 1, 2, 4, 5, 7, 8, 10, 12, 16, 20, etc.). In the description of shock wave catheters and electrodes below, a fluid-filled balloon is not depicted, though such a balloon may be included in any of the variations described herein.

In some variations, a single-layer shock wave electrode pair may comprise a first electrode comprising a protrusion and a second electrode comprising a recess that receives the protrusion, where a separation between the edge of the protrusion and the edge of the recess forms a spark gap. For example, the first electrode may comprise a recess and the second electrode may comprise a protrusion that is received by the recess such that the separation between the protrusion and the recess forms a spark gap. A spark gap is a separation between two electrodes across which a plasma arc is likely to form in the presence of a high voltage pulse across those electrodes. The protrusion and the corresponding recess may have any suitable geometry or shape, and may be, for example, shaped like a circle, oval, ellipse, square, hexagon, octagon, triangle, and the like. Protrusions and recesses may have corresponding arcuate shapes or curves. In some variations, the shape of the protrusion and the recess may be selected such that the separation between the first and second electrode is fairly uniform. For example, the protrusion may be circular, so that the distance between the edge of the circular protrusion to the edge of the recess in the second electrode that receives that protrusion may be substantially uniform. The shape of the protrusion and the recess may be selected such that the likelihood of a spark or arc forming at any location along the length of the spark gap is substantially the same. In some variations, the protrusion and the recess may be configured such that the likelihood of a spark forming between the protrusion and the recess is substantially uniform or equal along the length of the spark gap. For example, the protrusion and the corresponding recess may have a smooth contour (i.e., without acute angles, tight turns, or small radii of curvature) such as an arcuate or rounded curve. Arranging the electrodes such that the location of the spark along the spark gap is randomized may help to extend the life of the electrodes as compared to electrodes where the spark always occurs at the same location or region of the spark gap. By arranging the electrodes such that sparks originate at different locations along the gap, the wear on the electrode may be distributed along the gap instead of wearing down a single location along the gap. This may help to lengthen the life of the electrodes as compared to electrodes where sparks originate at the same location or region of the spark gap.

Some electrodes may have one protrusion on one side and one recess on another side (e.g., a protrusion on the proximal edge of the electrode and/or at a first radial position, a recess on the distal edge of the electrode and/or second radial position), and/or a first protrusion on one side and a second protrusion on another side (e.g., a first protrusion on the proximal edge of the electrode and/or at a first radial position, a second protrusion on the distal edge of the electrode and/or at a second radial position), and/or a first recess on one side and a second recess on another side (e.g., a first recess on the proximal edge of the electrode and/or at a first radial position, a second recess on the distal edge of the electrode and/or at a second radial position). In an electrode pair, the first electrode may comprise any number or combination of protrusions and/or recesses (such as those described above) while the second electrode may comprise a corresponding number or combination of recesses and/or protrusions that are complementary to the protrusions and/or recesses of the first electrode. In some variations where the first and second electrodes have more than one pair of complementary protrusions and/or recesses between them, a spark or arc may form between only one of the protrusion/ recess pairs at a time (e.g., per voltage pulse), and there may be some variability as to which of the protrusion/recess pairs will spark at a particular time. That is, the spark or arc will only happen at one of the protrusion/recess pairs, while the next spark or arc may be at another one of the protrusion/ recess pairs. This variability may help to distribute the wear across the multiple protrusion/recess pairs so that the overall life and/or durability of the electrode pair is extended as compared to an electrode pair where all of the sparks are formed across the same protrusion/recess pair. In some variations, the distal and/or proximal edges of the first electrode and the proximal and/or distal edges from the second electrode may have multiple undulating curves, lobes, peaks and troughs, such that the interface between them comprises a space (which may be a spark gap) that curves between the edges of the electrodes. The space between the two electrodes may have varying distances, which may in turn determine where a spark or plasma arc extends between the electrodes during the generation of a shock wave. For example, to reduce the likelihood that a spark occurs at a particular location between the two electrodes, the spacing at that location may be greater than the spacing in the surrounding areas. To increase the likelihood that a spark occurs at a particular location between the two electrodes, the spacing at that location may be less than the spacing in the surrounding areas. Examples of electrode pairs with varying degrees of separation are further described below.

Figure 1B:
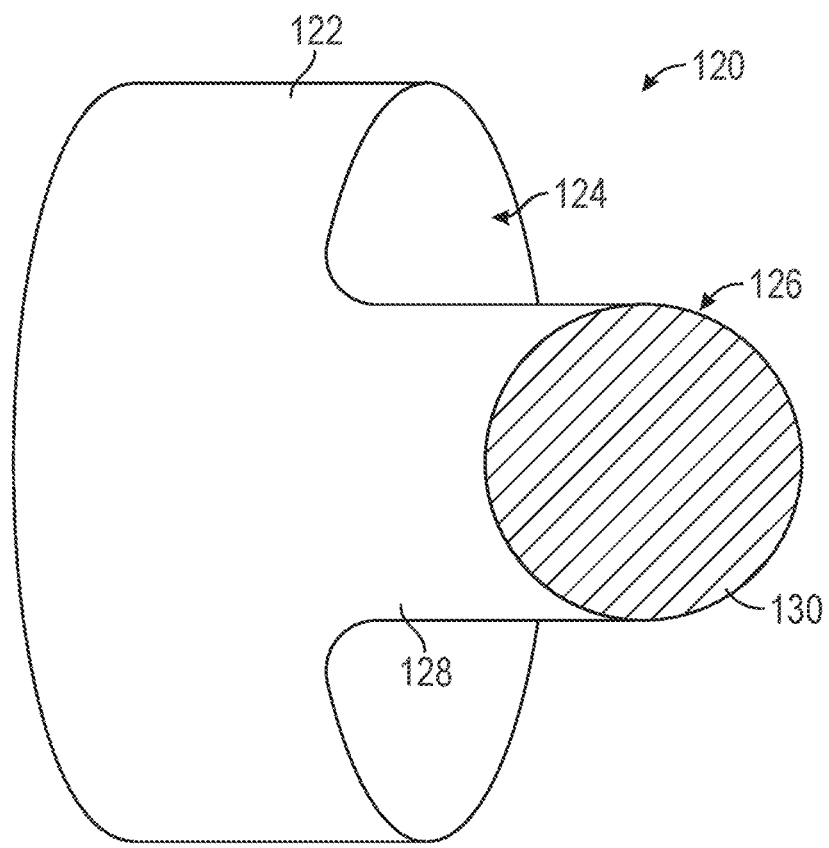
FIG. 1B depicts one variation of a single-layer electrode.

In some variations, the electrodes may be coated with an insulating material in certain regions and not coated with insulating material (i.e., electrically exposed) in other regions. The location of the insulated regions and exposed regions may also help to increase the likelihood of generating a plasma arc in certain regions while decreasing the likelihood of generating a plasma arc in other regions. For example, insulating the region of the electrodes where the separation between the electrodes is narrow (e.g., may be the narrowest separation) may help to greatly reduce the likelihood of generating a plasma arc across the separation in this region, while exposing (i.e., not insulating) this region may increase the likelihood of generating a plasma arc. The location of a spark gap may be determined at least in part by the relative locations of insulated regions and exposed regions of the electrodes, as well as the size of the spacing/ separation between the electrodes at the exposed regions. The location of spark gaps and the characteristics of the shock waves produced by the plasma arcs that span those spark gaps may be determined at least in part by the size, shape and location of the exposed regions of the electrodes. FIG. 1B depicts one variation of an electrode that may be used in any of the shock wave catheters described herein. Electrode 120 may be shaped as a cylindrical band configured to be disposed over the surface of an elongate member. Electrode 120 may comprise a sleeve 122 with a lumen 124 therethrough and a protrusion 126 extending from the sleeve 122. The protrusion 126 may have any of the shapes described and depicted herein, and in the variation of FIG. 1B, may comprise a stem portion 128 and a lobe 130 at the end of the stem. In this example, the shaded region of the lobe 130 may be exposed while the unshaded regions of the electrode 120 are covered by an insulating material. The lobe 130 may be the region of the electrode that interfaces with a recess of a second electrode that has exposed edges (e.g., may be substantially or entirely exposed), and the separation/spacing between the lobe and the edges of the recess may form a spark gap. Exposed or uninsulated regions of two electrodes in close proximity to each other may form a spark gap, regardless of the geometry of the electrodes. Optionally, the exposed regions of the electrodes may be treated (e.g., coated) to help enhance heat dissipation capabilities. For example, the exposed regions of any of the electrodes described herein may have a silver or gold coating. In the variations of shock wave catheters described below, the protrusions or recesses of one electrode and the complementary recesses or protrusions of an adjacent electrode that interfaces with the first electrode may have exposed regions of electrically conductive material to form a spark gap at those interfaces. Teflon, kapton, varnish or oxides and anodized insulations are just a few examples of many suitable insulation materials.

Figure 1C:
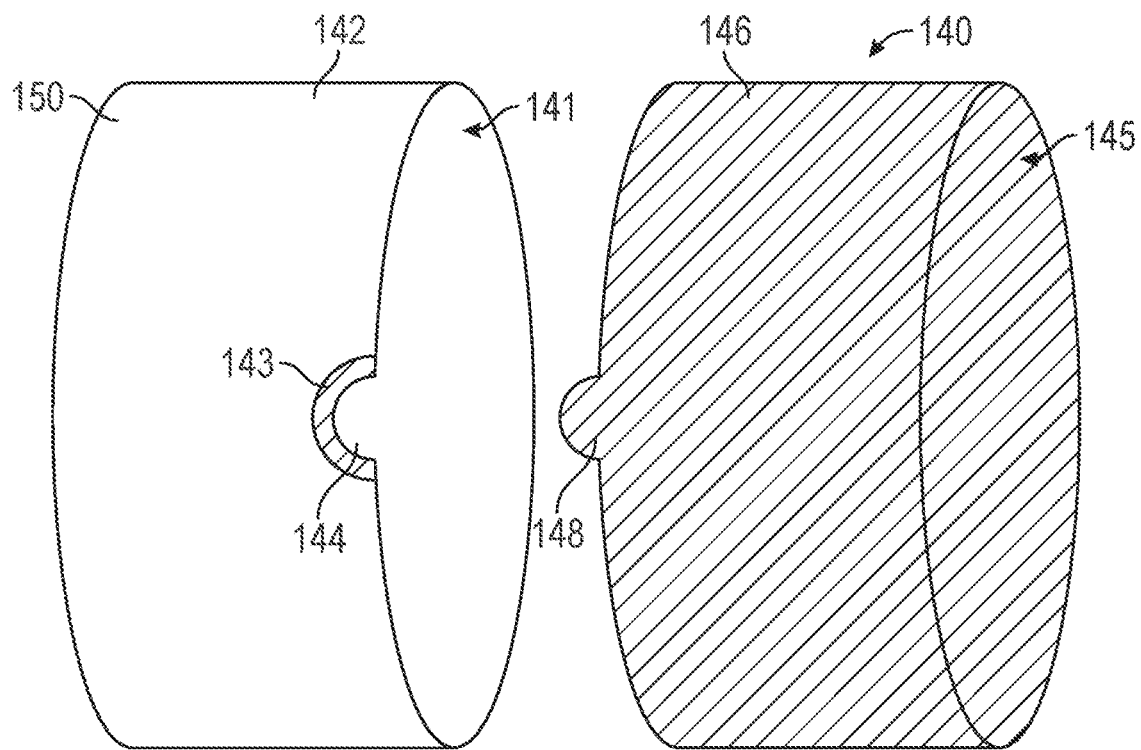
FIG. 1C depicts one variation of a pair of single-layer electrodes.
Figure 1D:
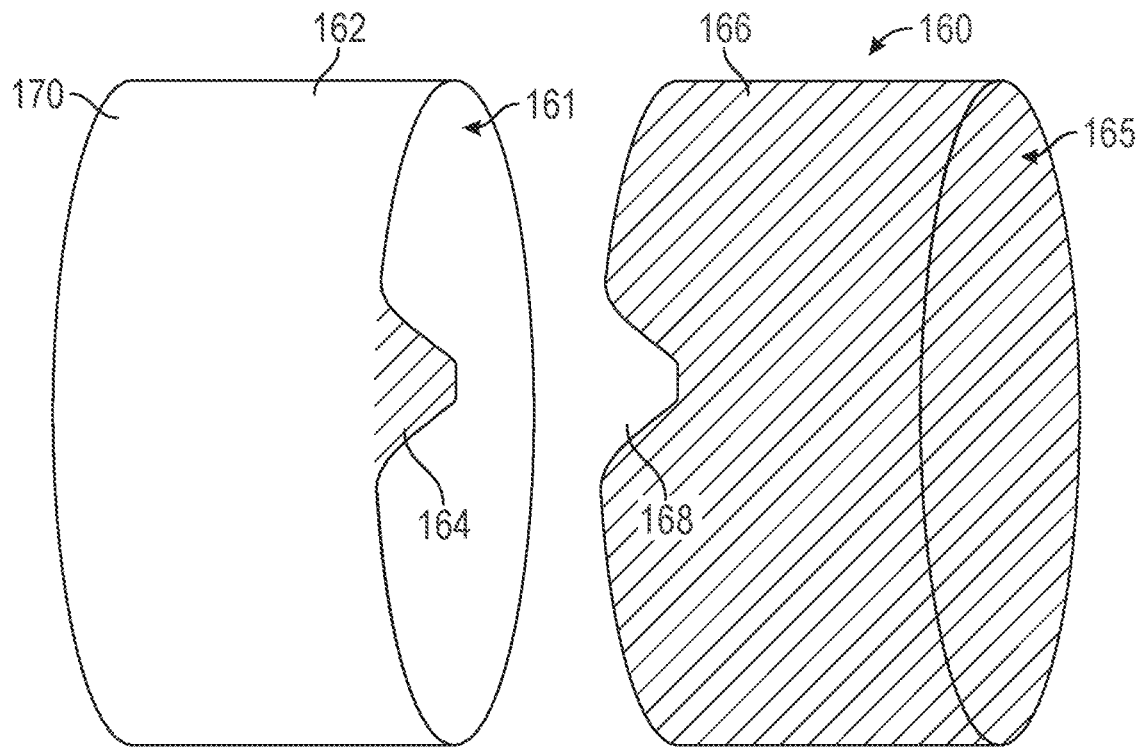
FIG. 1D depicts another variation of a pair of single-layer electrodes.

The relative surface area of the exposed regions of an electrode pair may also increase or decrease the likelihood of a spark or arc forming across the spacing/separation between electrodes. For example, the first electrode may have a first exposed region with a first surface area and the second electrode may have a second exposed region with a second surface area, and in some variations, the second surface area may be greater than the first surface area. For example, the ratio between the first surface area and the second surface area may be from about 1:2 to about 1:50, e.g., from about 1:2 to about 1:10, from about 1:4 to about 1:10, from about 1:2 to about 1:20, from about 1:10 to about 1:30, from about 1:20 to about 1:40, from about 1:30 to about 1:50. For example, the area of the first surface area (e.g., of the electrode with the smaller exposed region) may have a radius of about 0.008 inch, and the ratio between the first surface area and the second surface area may be about 1:4. FIG. 1C depicts one variation of an electrode pair 140 comprising a first electrode 142 having a recess 144 and a second electrode 146 having a protrusion 148 that corresponds with the recess 144. In this example, the recess and protrusion both have arcuate shapes. The first electrode 142 and second electrode 146 may be tubular, each with a lumen 141, 145 therethrough configured to be disposed over the surface of an elongate member such that they are coplanar (e.g., in a single layer). The shaded/patterned portions of the electrodes represent electrically exposed (i.e., uninsulated) regions of the electrodes and the unshaded portions represented electrically insulated regions. While the entire surface of the second electrode 146 may be exposed, a small region 143 of the first electrode 142 located around the edge of the recess may be exposed. The surface of the small region 143 is smaller than the surface area of the second electrode, and the ratio between them may be any of the ratios described above. FIG. 1D depicts another variation of an electrode pair 160 comprising a first electrode 162 having a protrusion 164 and a second electrode 166 having a recess 168 that corresponds with the protrusion 164. In this example, the protrusion and the recess both have arcuate shapes. The first electrode 162 and second electrode 166 may be tubular, each with a lumen 161, 165 therethrough configured to be disposed over the surface of an elongate member such that they are coplanar (e.g., in a single layer). While the entire surface of the second electrode 166 may be exposed, only the protrusion 164 of the first electrode may be exposed. The surface of the protrusion 164 is smaller than the surface area of the second electrode, and the ratio between them may be any of the ratios described above. Other variations with different areas and shapes of insulated and exposed electrode regions are described and depicted herein.

Figure 2A:
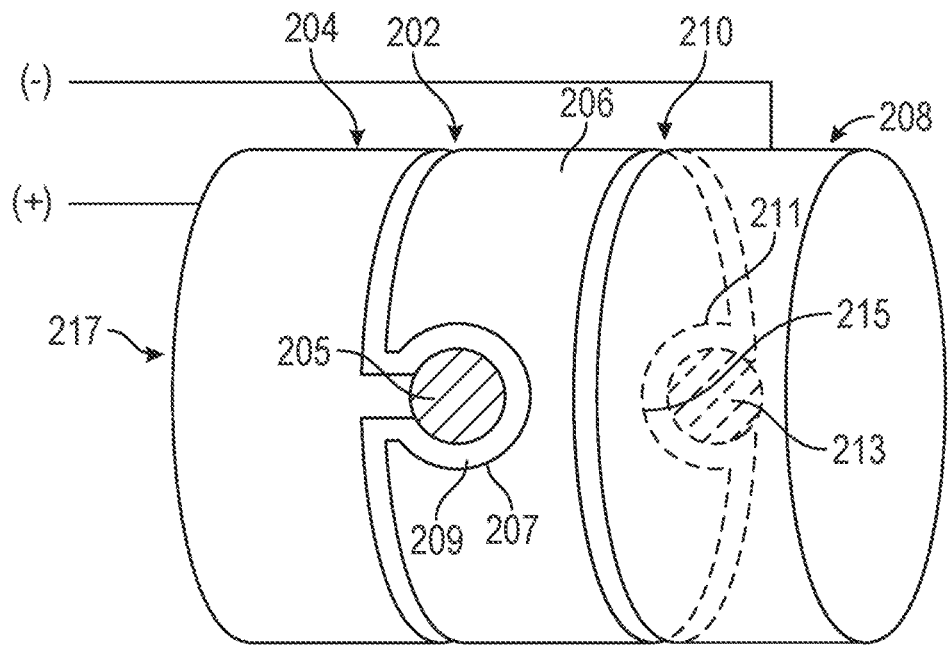
FIG. 2A depicts one variation of single-layer electrodes of a shock wave catheter that interfit with each other.

FIG. 2A depicts one example of two electrode pairs, where one electrode (e.g., the middle electrode) is a part of both pairs. The first electrode pair 202 may comprise a first electrode 204 and a second electrode 206, and the second electrode pair 210 may comprise the second electrode 206 and a third electrode 208. The first electrode 204 may be electrically connected to the positive terminal of a voltage generator while the third electrode 208 may be electrically connected to the negative terminal of a voltage generator (e.g., by a wire for each connection). The first, second, and third electrodes may be ring-shaped and have a lumen 217 therethrough, and be disposed over the surface of an elongate body on a single-layer (i.e., the electrodes may be co-planar with each other over the surface of the elongate body). The first electrode 204 (i.e., the proximal electrode) may comprise a protrusion 205 that has a stem and a circular lobe. The second electrode 206 may comprise a recess 207 that is sized and shaped to receive the protrusion 205 such that there is a space or gap 209 between the edge of the protrusion 205 and the edge of the recess 207. The second electrode 206 and third electrode 208 may have a similar interface on the opposite side of the system. That is, the second electrode 206 may have a second recess 211 and the third electrode 208 may have a protrusion 213 that is received by the second recess 211 such that there is a space or gap 215 between them. The protrusion 213 may have a stem and a circular lobe similar in size and shape to the protrusion 205, or may have a different size or shape, as may be desired. The circular lobes of the protrusions 205, 213 and the edges of the recesses that receive the protrusions (recesses 207, 211) may be electrically exposed or conductive, while the remainder of the electrodes may be electrically insulated. In this variation, the entire surface of the second electrode 206 may be exposed or uninsulated. As such, spark gaps may be formed at the interfaces of the protrusions and the recesses. The location of the first protrusion 205 and corresponding recess 207 and the location of the second protrusion 213 and corresponding recess 211 may vary according to the desired initiation location of a shock wave. In this example, the first pair and second pair of protrusions/recesses are located radially opposite to each other, with the first pair located on a proximal edge of the electrode and the second pair located on a distal edge of the electrode. In other variations, the first and second pair may both be located on the proximal side (or the distal side) of the middle electrode 206, but radially opposite each other. In some variations, the first and second pair may be radially offset with respect to each other, where the offset angle may be anywhere from about 30 degrees to about 180 degrees in either direction (clockwise or counterclockwise). In some variations, there may be more than one pair of protrusions/recess between each electrode pair. For example, the first electrode 204 may have an additional protrusion or recess at a different radial location and the second electrode 206 may have an additional corresponding recess or protrusion.

Optionally, different regions of each of the electrodes may be covered by an insulating material while other regions are exposed. For example, the portions of the protrusion 205 and the protrusion 213 that are shaded may be exposed, while the remainder of the electrode 204 and the electrode 208 may be covered by an insulating material. The second electrode 206 may be entirely exposed and uninsulated. Alternatively, at least the regions around the edges of the recesses 207 and 211 may be exposed, while the remainder of the electrode may be insulated. The exposed regions may optionally have a silver or gold coating. As described previously, the relative sizing of the surface area of the exposed regions between the electrodes in a pair may help to facilitate and guide the electric current flow between electrodes so that plasma arcs or sparks occur at the desired spark gap location. In some variations, the likelihood of creating a plasma arc that is capable of generating a shock wave is increased when the surface area of the exposed (i.e., uninsulated) region of a first electrode is smaller than the surface area of the exposed region of a second electrode that is adjacent to it. The exposed surface area differential may be represented by the ratio of the surface area of an exposed region of a first electrode to the surface area of an exposed region of a second electrode. The interface between the electrodes of a pair described in any of the shock wave catheters disclosed herein, regardless of their shape or location, may have the exposed surface area differential described above.

Figure 2B:
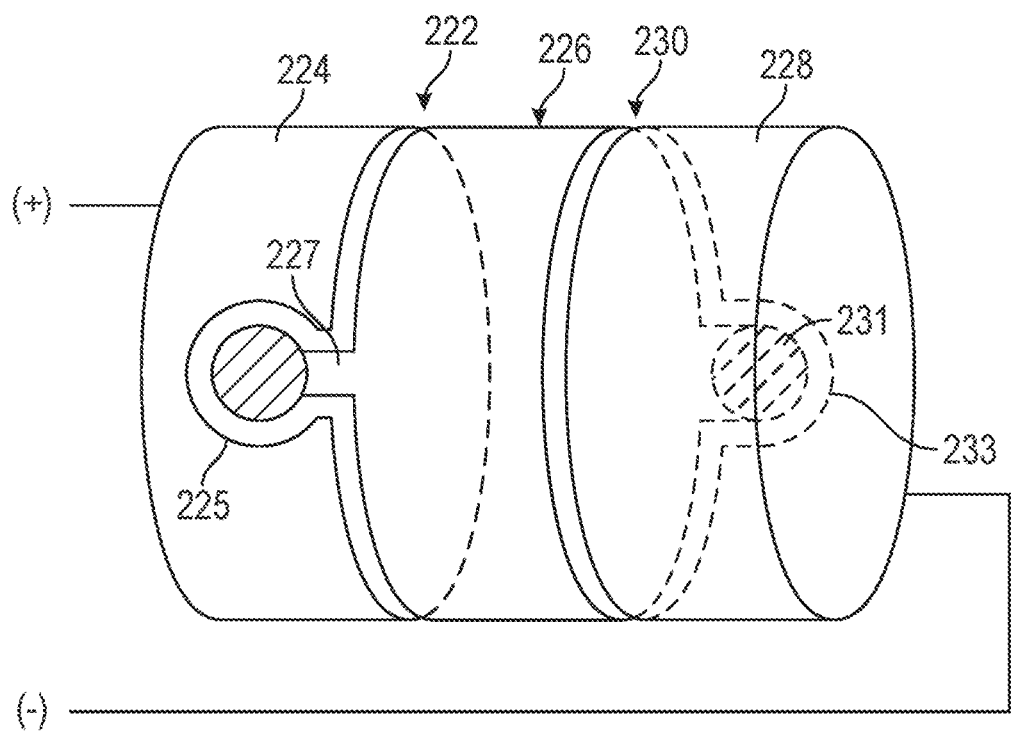
FIG. 2B depicts another variation of single-layer electrodes of a shock wave catheter that interfit with each other.

FIG. 2B depicts another variation of two electrode pairs that are similar to the electrode pairs depicted in FIG. 2A, except that where there was a protrusion, there is now a recess and where there was a recess, there is now a protrusion. For example, the first electrode pair 222 comprises a first (proximal) electrode 224 and a second (middle) electrode 226. The first electrode 224 comprises a recess 225. The second (middle) electrode 226 comprising a protrusion 227 that is located within the recess 225. The second electrode pair 230 comprises the second electrode 226 and a third (distal) electrode 228. The second electrode 226 comprises a second protrusion 231. The third (distal) electrode 228 comprises a recess 233 within which the protrusion 231 is located. In other words, instead of the middle electrode having two radially offset and opposite recesses as illustrated in FIG. 2A, the middle electrode now has two radially offset and opposite protrusions as illustrated in FIG. 2B. The first electrode 224 may be connected to the positive terminal of a voltage generator while the third electrode 228 may be connected to the negative terminal of a voltage generator (e.g., by a wire for each connection). The various parameters and variants described above for FIG. 2A may also be applicable in the variation depicted in FIG. 2B.

Figure 2C:
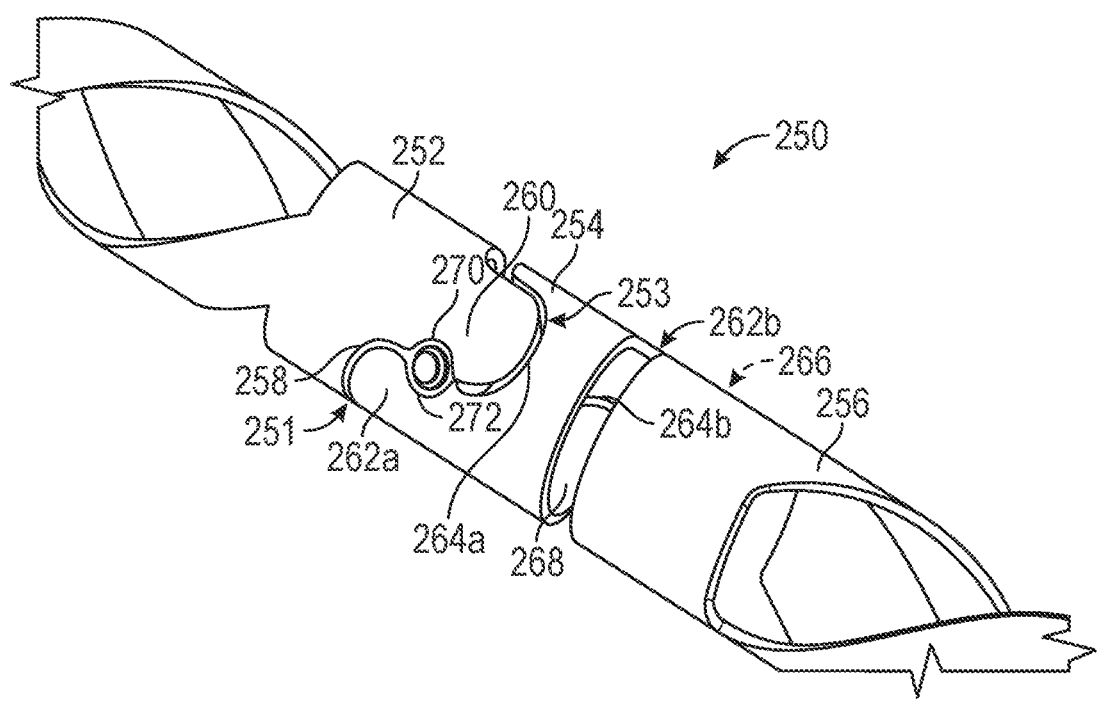
FIG. 2C depicts one variation of three single-layer electrodes (i.e., two electrode pairs) that have multiple spark gaps per electrode pair.

FIG. 2C depicts an example of a shock wave catheter 250 comprising a first electrode 252, second electrode 254, and third electrode 256 (for clarity, the elongate body, guide wire lumen, and wiring of the catheter 250 are not shown). The first, second and third electrodes are coplanar with each other, arranged on a single layer along the surface of the elongate body of the catheter. The first electrode 252 may comprise a first recess 258 and a first protrusion 260. The second electrode 254 may comprise a second protrusion 262a, a second recess 264a, a third protrusion 262b opposite to the second protrusion 262a, and a third recess 264b opposite to the second recess 264a. The third electrode 256 may comprise a fourth recess 266 and a fourth protrusion 268. There may be two spark gaps located between the first and second electrodes, and two other spark gaps located between the second and third electrodes. In some variations, of the two spark gaps between an electrode pair, only one spark gap will form a plasma arc during a voltage pulse. The location and arcuate curvature of the first recess 258 may correspond with the location and arcuate curvature of the second protrusion 262a to form a first spark gap 251 therebetween, and the location and arcuate curvature of the first protrusion 260 may correspond with the location and arcuate curvature of the second recess 264a to form a second spark gap 253 therebetween. Similarly, the location and arcuate curvature of the third recess 264b may correspond with the location and arcuate curvature of the fourth protrusion 268 to form a third spark gap 255 therebetween, and the location and arcuate curvature of the third protrusion 262b may correspond with the location and arcuate curvature of the fourth recess 266 to form a fourth spark gap therebetween (not visible in this view). While it may be desirable that some regions of the separation between the electrodes (i.e., the protrusions and recesses) form spark gaps where the likelihood of plasma arc formation is relatively high, there may be some electrode separation regions where it is desirable for the likelihood of plasma arc formation to be relatively low. One way of reducing the likelihood of forming a plasma arc at a particular separation region is to increase the distance between the two electrodes relative to the surrounding separation region. An example is depicted in FIG. 2C. The first electrode 252 comprises a recess or groove 270 and the second electrode 254 comprises a recess or groove 272 that is aligned with the groove 270 of the first electrode 252. Aligning two recesses or grooves may increase the width of the separation between the first electrode 252 and second electrode 254 relative to the width of the separation in the intended spark gap regions. In some other variations, a first electrode may have a recess while the second electrode may have a straight edge (e.g., no protrusion) in the region of the recess. While the recesses are depicted as having an arcuate or curved shape, it should be understood that the recesses may have any shape. For example, a recess may have straight edges (e.g., a square shape, rectangular shape, triangular shape, etc.), and/or have curved edges (e.g., circle, oval, ellipse, semi-circle, semi-oval, semi-ellipse, etc.), and/or a combination of straight and curved edges (e.g., rectangular, triangular or any polygon with rounded corners and/or undulating edges). The increased separation between the electrodes provided by one or more recesses may help to reduce the likelihood of formation of a plasma arc at the recessed region(s). In some variations, one or both of the electrodes in a pair may have edge(s) that curve away from the edge of the other electrode. For example, the electrodes may have an undulating curved edge (comprising one or more concave or convex curves) where the peaks and troughs do not follow each other (e.g., are out-of-phase with each other). For example, one electrode may have a straight edge (i.e., without a recess or protrusion), while the other electrode may have undulating curves comprising a convex curve at a desired spark gap region and a concave curve in regions where no spark gap is desired. Alternatively or additionally to increasing the separation width in a region where no plasma arc is desired, such regions may be electrically insulated, which may also help to impede the formation of a plasma arc.

Figure 3A:
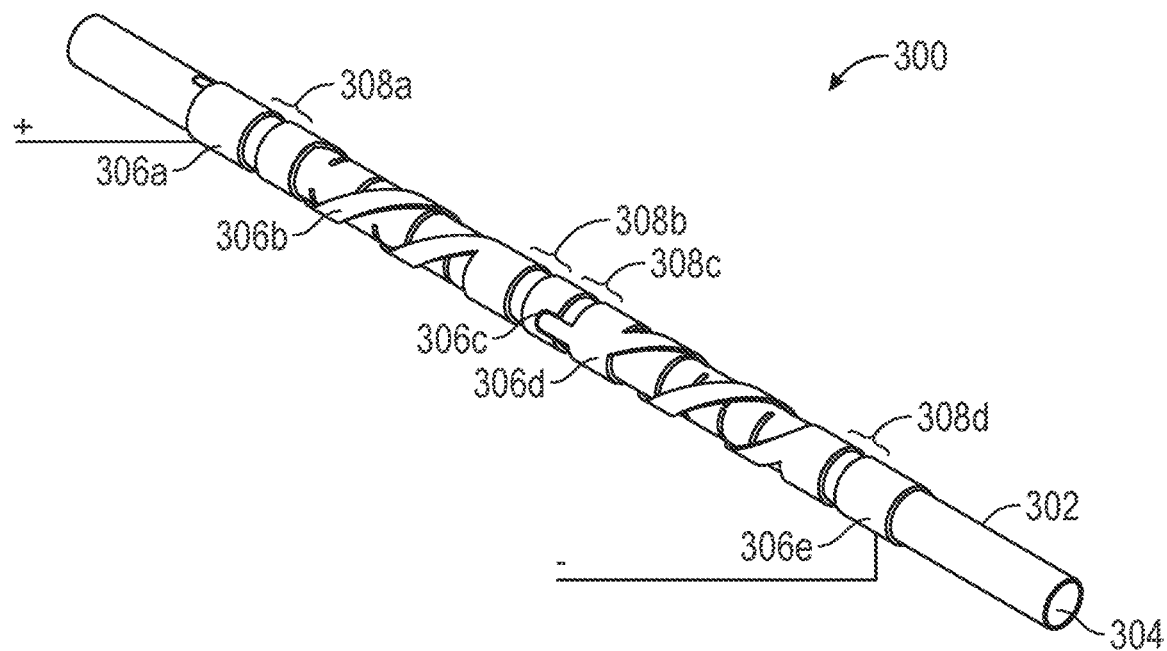
FIG. 3A is a perspective view of one variation of a shock wave catheter (balloon not shown).
Figure 3B:
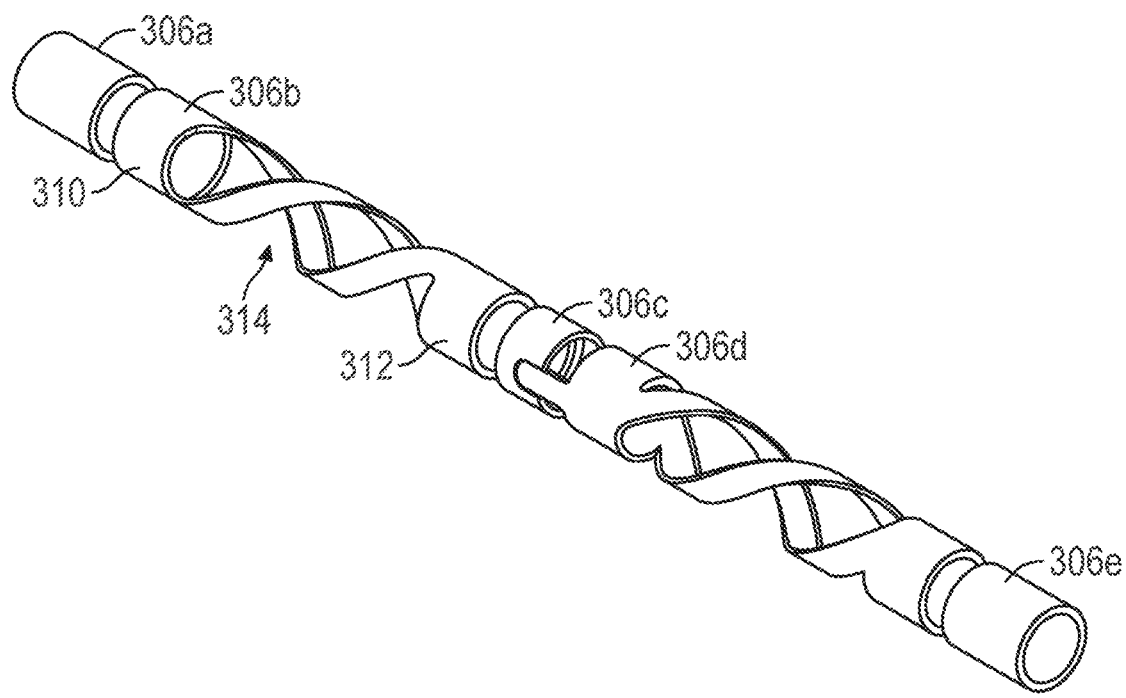
FIG. 3B is perspective view of the single-layer electrodes of the shock wave catheter of FIG. 3A.

One variation of a shock wave catheter system having one or more single-layer electrodes is depicted in FIGS. 3A-3D. The shock wave catheter 300 may comprise an elongate member 302, a guide wire lumen 304, and five electrodes 306a,b,c,d,e that form four electrode pairs 308a,b,c,d. The shock wave catheter 300 may also comprise a balloon (e.g., an angioplasty balloon) that encloses the electrodes (not shown), a first wire that connects the proximal-most electrode 306a to a positive terminal of a voltage source and a second wire that connects the distal-most electrode 306e to a negative terminal of a voltage source. As previously described, the balloon is filled with a fluid medium before a voltage is applied across the electrodes for the generation of shock waves. The first and second wires may each extend along the surface and/or lumen and/or within the wall of the elongate member 302. In some variations, the wires may extend along interior walls of the guide wire lumen 304. Each electrode pair may have one or more spark gaps as may be desirable. For example, a first electrode pair may have one spark gap capable of initiating one shock wave, while a second electrode pair may have two spark gaps capable of initiating two shock waves (i.e., one shock wave per spark gap). In other examples, an electrode pair may have more than two spark gaps, and may have three, four, five or more spark gaps. When a voltage is applied across the proximal-most electrode 306a and the distal-most electrode 306e, a series of plasma arcs may form serially across the spark gaps between the electrodes (i.e., from electrode 306a to electrode 306b, from electrode 306b to electrode 306c, from electrode 306c to electrode 306d, from electrode 306d to electrode 306e, which then guides the current back to the negative terminal of the voltage source via the wire) to initiate a series of expanding shock waves. The number of initiated shock waves may correspond to the number of spark gaps between the electrodes (e.g., each spark gap gives rise to one plasma arc per voltage pulse and/or each plasma arc initiates one shock wave), and/or may be greater than (e.g., a spark gap may give rise to more than one plasma arc per voltage pulse, and/or each plasma arc initiates one or more shock waves) or less than (e.g., plasma arcs may not form across all of the spark gaps) the number of spark gaps. FIG. 3B depicts the electrodes 306a,b,c,d,e without the elongate member 302. The length of each electrode with respect to each other may vary. For example, the proximal-most electrode 306a and the distal-most electrode 306e may be shorter than the second electrode 306b and fourth electrode 306d. The shortest electrode may be the center electrode 306c. Electrodes whose lengths extend along a substantial segment of the elongate member may be configured such that their effect on the flexibility and bendability of the elongate member is reduced. For example, electrode 306b (as well as electrode 306d) may comprise a proximal portion (e.g., a band) 310, a distal portion (e.g., a band) 312, and a body portion 314 extending between the proximal and distal portions. In this variation, the proximal and distal portions may be generally cylindrical or marker band-like structures. The body portion may be covered by an insulating material, which may help to facilitate current flow between the proximal and distal portions along the body portion. The structure of the body portion 314 may be selected to help facilitate bending of the electrode 306b as the elongate body 302 bends. In the variation depicted in FIGS. 3A-3C, the body portion 314 may comprise a helical structure or spiral that wraps around the surface of the elongate body 302 between the proximal and distal portions. The threads of the helical structure or spiral of the body portion 314 may be selected in order to accommodate flexion, torqueing, and/or steering of the shock wave catheter. For example, the body portion 314 may have a pair of spirals (e.g., a double-helix), where each spiral has one twist. In other variations, there may be more spirals (e.g., triple or quadruple helices), and/or each spiral may have more than one twist (e.g., two, three, four, five or more twists).

Figure 3C:
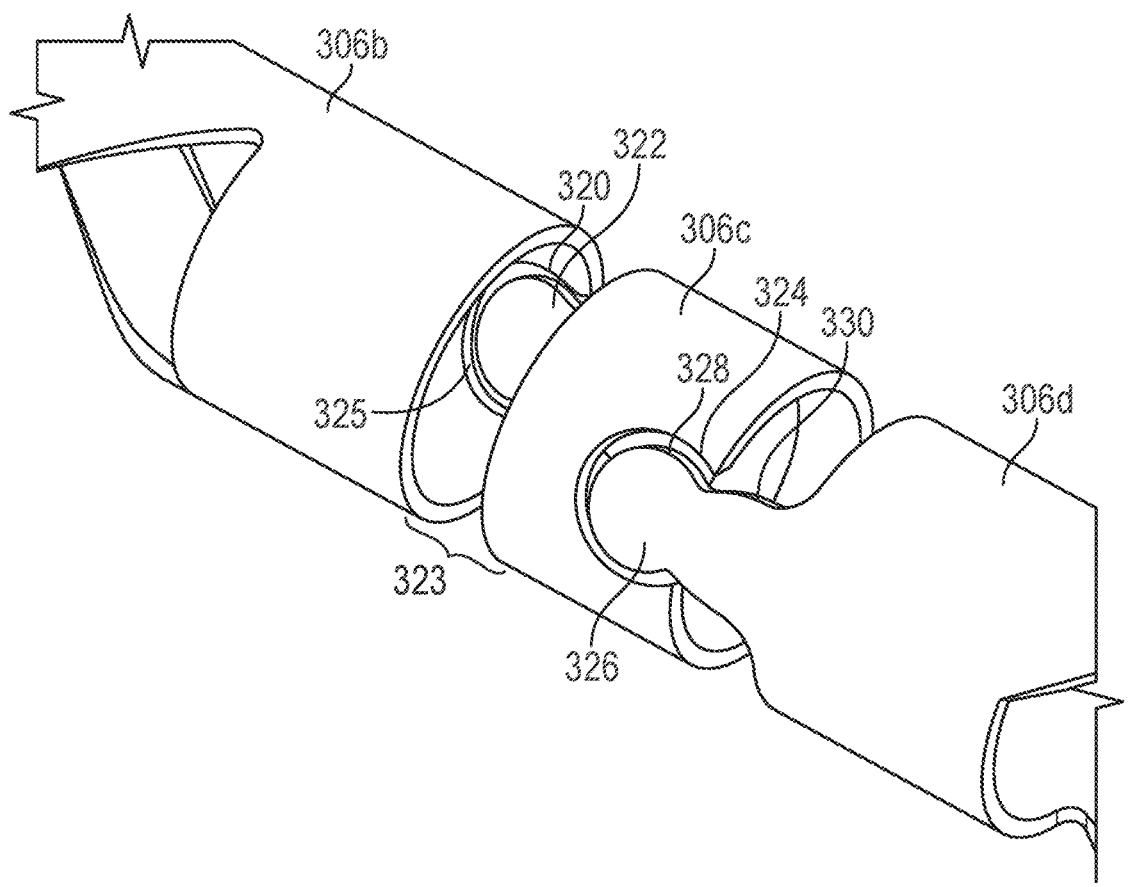
FIG. 3C is a close-up view of three single-layer electrodes of the shock wave catheter of FIG. 3A.

FIG. 3C is a close view of the interface between electrodes 306b,c,d. In this variation, electrode 306b has a recess 320 that corresponds to a protrusion 322 on electrode 306c (which form electrode pair 308b), and electrode 306c has a recess 324 that corresponds to protrusion 326 on electrode 306d (which form electrode pair 308d). There may be a separation 323 between electrodes 306b and 306c, where the narrowest portion of the separation 323 may be a spark gap 325. In this variation, the protrusions 322, 326 may have a circular lobular portion 328 connected to a stem 330. The stem 330 may extend between the widest part of the separation 323 between the electrodes, while the perimeter of the circular lobular portion 328 may comprise at least a portion of the spark gap 323. In this example, the protrusions and recesses for both electrode pairs have the same or similar shape and size, however, in other variations, the protrusions and recesses may have different shapes or sizes.

The electrodes 306b,c,d may have electrically insulated regions and exposed (i.e., electrically non-insulated) regions, the location and sizing of which may be configured to help guide the direction of the current flow and/or to facilitate the formation of plasma arcs or sparks at the desired spark gap locations. In the variation depicted in FIG. 3C, the majority of the surface area of the electrode 306b may be exposed or uninsulated, while the majority of the surface area of the electrode 306c is insulated, except for the regions that are adjacent to the spark gap 325. That is, the protrusion 322 (e.g., the circular lobe of the protrusion) and the region along the edge of the recess 324 of the electrode 306c may be exposed, but the remainder of the electrode 306c may be insulated (e.g., the stem portion of the protrusion, the cylindrical region or body of the electrode extending between the proximal and distal portions or bands of the electrode, the spiral or twisted region of the body, the body region between the proximal and distal portions or bands of the electrode, etc.). The circular lobular portion 328 of the electrode 306d may be exposed, while the stem portion 328 and the body of the electrode (e.g., the portion extending between the proximal and distal ends) may be insulated. The surface area of the exposed portion the electrode 306b may be larger than the surface area of the protrusion 322 that is exposed. For example, the ratio between the surface area of the exposed portion may be from about 1:2 to about 1:50, e.g., from about 1:2 to about 1:10, from about 1:2 to about 1:20, from about 1:10 to about 1:30, from about 1:20 to about 1:40, from about 1:30 to about 1:50. Similarly, the surface area of the circular lobular portion 328 may be smaller than the surface area of the exposed region along the edge of recess 324, and may have similar ratio values described above. Some variations of electrodes may have a proximal portion with an exposed protrusion or recess edge, a distal portion with another exposed protrusion or recess edge, and a body portion between the proximal and distal portions that is insulated. The surface area of the one or more exposed regions of an electrode may affect the strength, shape, location, etc. of the plasma arc formed, which in turn affects the sonic output and/or direction of the initiated shock wave.

EXPERIMENTAL DATA AND RESULTS

An experiment was conducted with a prototype of the shock wave catheter depicted and described in FIGS. 3A-3C. FIGS. 4A and 4B are tables that represent the sonic output of shock wave generated across the electrodes depicted in FIGS. 3A-3C. In this experiment, the shock wave electrodes were located in the center of a 2.5 mm×25 mm L2140 balloon filled with saline solution at a pressure of 4 ATM. The magnitude of the generated sonic output was measured 2 microseconds from the initiation time of the plasma arc or spark. The propagation distance of a shock wave at this time delay is about 3 mm. The voltage pulse width was 1 microsecond, with a magnitude of 3000 volts. The diameter of the wires that connected the electrodes to the positive and negative terminals of the voltage source was 0.005 inch and the length was about 170 cm. Insulated portions of the wire were covered with a polyimide insulation layer with a thickness of 0.0005 inch. Two spark gap sizes were tested by measuring the sonic output of the generated shock waves. The table of FIG. 4A depicts sonic output data from an electrode pair with a spark gap of about 0.003 inch. The table of FIG. 4B depicts sonic output data from an electrode pair with a spark gap of about 0.004 inch. Based on this set of experiments, a smaller spark gap (e.g., with a smaller width) may give rise to shock waves with higher sonic output than a larger spark gap.

Figure 5:
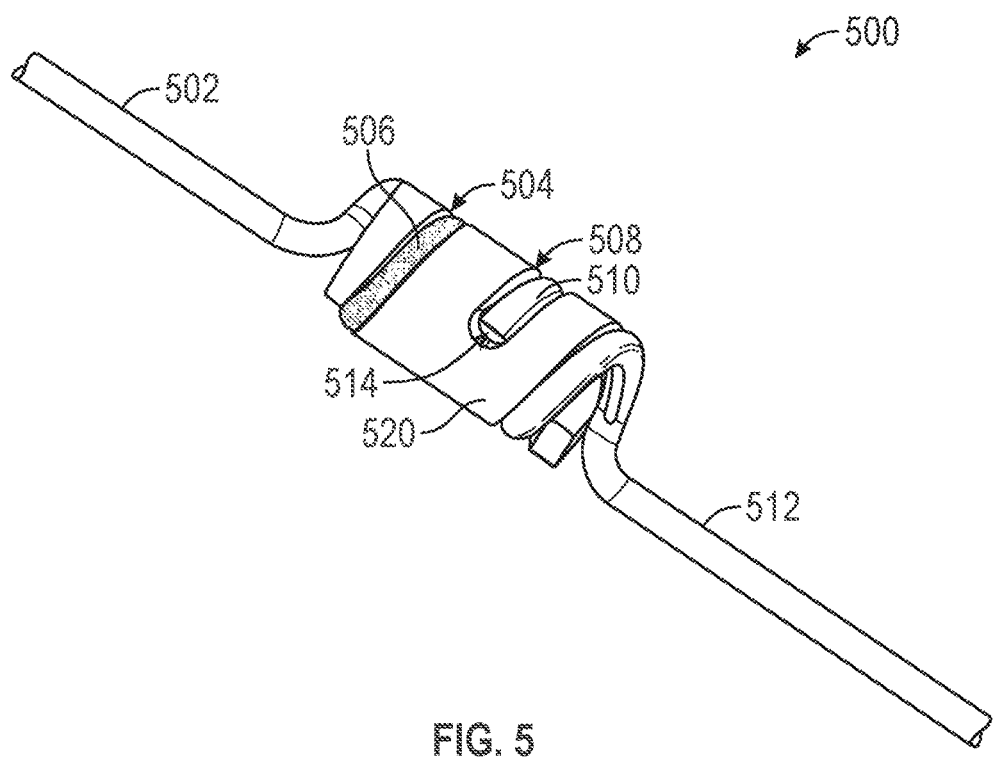
FIG. 5 depicts a prospective view of one variation of an electrode pair comprising a band.

FIG. 5 depicts a prospective view of an electrode pair comprising a band. As shown in FIG. 5, in one variation, an electrode pair 500 may comprise a first electrode and a second electrode. The first electrode may comprise band 520. The second electrode may comprise a portion of a wire 512 that is exposed or uninsulated. In one variation, the wire 502 may be electrically coupled to a positive terminal of a voltage source, and the wire 512 may be electrically coupled to a negative terminal of the voltage source, or vice versa. The wire portion 506 (e.g., a portion of the wire 502) and the wire portion 510 (e.g., a portion of the wire 512) may be coupled using a band 520. The band 520 may comprise one or more grooves, such as a first groove 504 and a second groove 508. In some variations, the first groove 504 may have a dimension (e.g., width) that is smaller than the corresponding dimension of the second groove 508. As a result, the wire portion 506 may be snuggly disposed in the first groove 504 and the wire portion 510 may be loosely disposed in the second groove 508. The wire portion 510 may be loosely disposed in groove 508 to prevent shorted circuit between the wire portion 510 and the band 520. This feature also maintains the spark gap as the wire portion 510 erodes away.

As shown in FIG. 5, the wire 502 may comprise the wire portion 506 that is disposed in the first groove 504. In some variations, the wire 502 is insulated with an uninsulated or exposed section (e.g., wire portion 506). The wire portion 506, which is exposed or uninsulated, may be snuggly disposed in groove 504 to have a good electrical connection between the wire 502 and the band 520 (no spark in this region). The band 520 thus forms the first electrode. The wire 512 may comprise the wire portion 510 disposed in the second groove 508 of band 520. In some variations, the wire 512 and the wire portion 510 are insulated, and insulation is removed at the end or tip of the wire portion 510 to form a spark gap 514. The exposed or uninsulated portion of wire portion 510 thus forms the second electrode. The spark gap 514 separates the first electrode (e.g., band 520) and the second electrode (e.g., the exposed or uninsulated end or tip of wire portion 510). As described, the surface area of the one or more exposed regions of the first and second electrodes may affect the strength, shape, location, etc. of the plasma arc formed, which in turn affects the sonic output and/or direction of the initiated shock wave. The increase or decrease of the separation between the first and second electrodes may also increase or decrease the likelihood of formation of a plasma arc at the spark gap.

Figure 6:
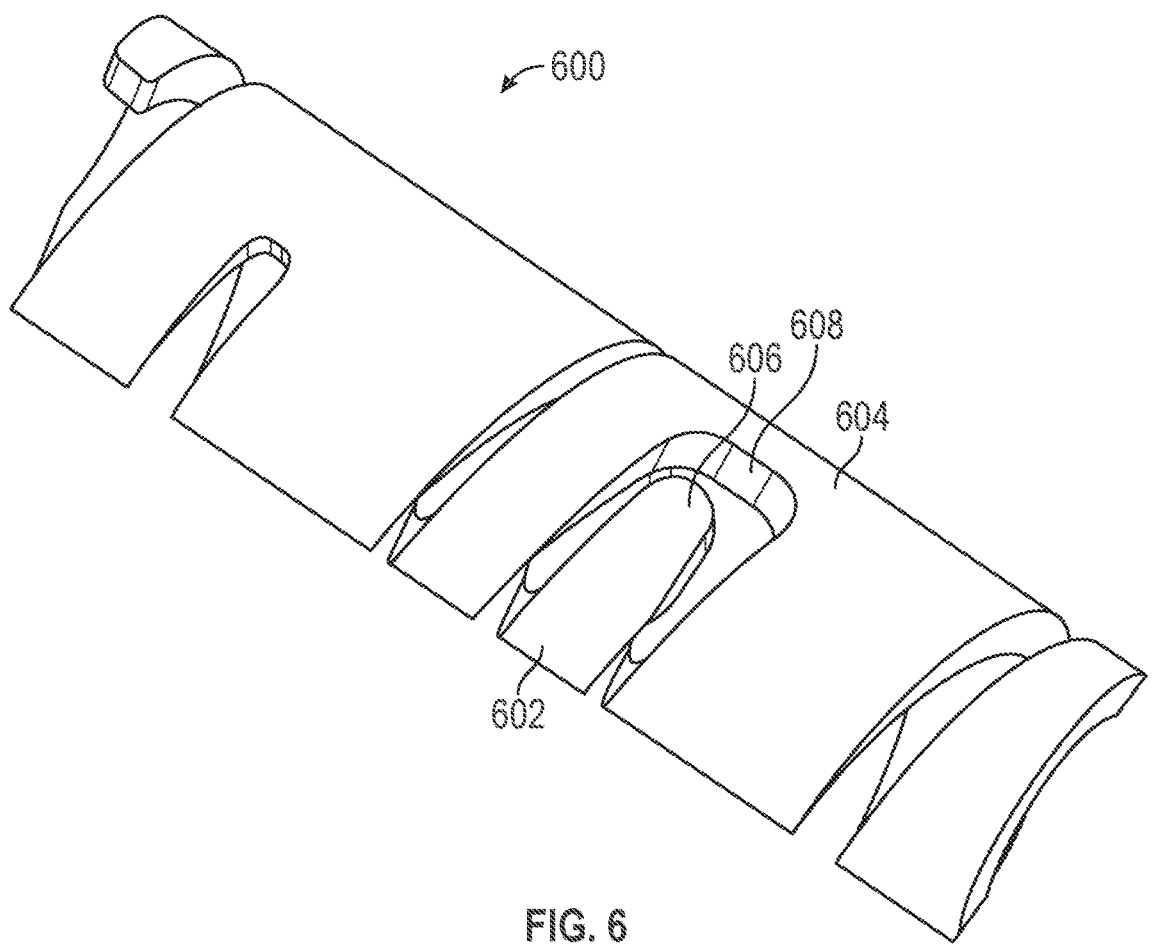
FIG. 6 depicts a prospect view of one variation of an electrode pair.

FIG. 6 depicts a prospective view of one variation of an electrode pair. As shown in FIG. 6, in one variation, an electrode pair 600 comprises a first electrode 602 and a second electrode 604. The first electrode 602 and the second electrode 604 may be shaped as a cylindrical band configured to be disposed over the surface of an elongate member. The first electrode 602 may comprise a protrusion (e.g., a tongue) 606; and the second electrode 604 may comprise a recess (e.g., a groove) 608. As shown in FIG. 6, the protrusion 606 and the recess 608 may be oriented perpendicular to the axis of the first electrode 602 and the second electrode 604, respectively. The protrusion 606 and the recess 608 may have corresponding arcuate shapes or curves. The protrusion 606 and the corresponding recess 608 may have any suitable geometry or shape, and may be, for example, shaped like a circle, oval, ellipse, square, hexagon, octagon, triangle, and the like.

In some variations, the first electrode 602 may be electrically coupled to a positive terminal of a voltage source, and the second electrode 604 may be electrically coupled to a negative terminal of the voltage source, or vice versa. In one variation, the surface area of the protrusion 606 (e.g., a tongue) may be electrically insulated using a polyimide coat except the end or tip region of the protrusion 606. The surface area of recess 608 may also be electrically insulated using a polyimide coat except the end region of the recess 608 (e.g., the groove area). Thus, the end or tip region of the protrusion 606 and the end region of the recess 608 are exposed to enable the generating of a spark. As described, the surface area of the one or more exposed regions of the first and second electrodes may affect the strength, shape, location, etc. of the plasma arc formed, which in turn affects the sonic output and/or direction of the initiated shock wave. The increase or decrease of the separation between the first and second electrodes may also increase or decrease the likelihood of formation of a plasma arc at the spark gap. In one variation, the insulation (e.g., the polyimide coating) of the protrusion 606 and the recess 608 may erode away after repeated spark generation. The erosion of the insulation may expose additional areas and thus increase or maintain the spark generation.

It will be understood that the foregoing is only illustrative of the principles of the invention, and that various modifications, alterations and combinations can be made by those skilled in the art without departing from the scope and spirit of the invention. Any of the variations of the various shockwave devices disclosed herein can include features described by any other shockwave devices or combination of shockwave devices herein. Furthermore, any of the methods can be used with any of the shockwave devices disclosed. Accordingly, it is not intended that the invention be limited, except as by the appended claims. For all of the variations described above, the steps of the methods need not be performed sequentially.

What is claimed is:

1. A treatment catheter comprising:
an axially extending elongate member;
a first cylindrical conductive band mounted on the elongate member;
a second cylindrical conductive band mounted on the elongate member in a distal position relative to the first cylindrical conductive band and arranged such that longitudinal spacing between the first cylindrical conductive band and the second cylindrical conductive band defines at least one spark gap between the first and second cylindrical conductive bands;
a first wire having a first end electrically connectable to a voltage source and having a second end in electrical communication with the first cylindrical conductive band;
a second wire having a first end electrically connectable to the voltage source and having a second end in electrical communication with the second cylindrical conductive band; and
a tube connected to the elongate member and surrounding the first and second cylindrical conductive bands, the tube being fillable with a conductive liquid,
wherein the first and second cylindrical conductive bands are configured such that a voltage pulse applied across the first and second wires causes a current to flow across the spark gap between the first and second cylindrical conductive bands and generate a shock wave in the liquid.

2. The catheter of claim 1, wherein the distal end of the first cylindrical conductive band comprises a circumferential side edge.

3. The catheter of claim 1, wherein the proximal end of the second cylindrical conductive band comprises a circumferential side edge.

4. The catheter of claim 1, wherein the distal end of the first cylindrical conductive band and the proximal end of the second cylindrical conductive band are located along the same cylindrical layer.

5. The catheter of claim 1, wherein either or both of the first cylindrical conductive band and the second cylindrical conductive band are formed from a hypotube.

6. The catheter of claim 1, further comprising:
a third cylindrical conductive band, positioned distal to the second cylindrical conductive band, and a third wire electrically connecting the third cylindrical conductive band to the voltage source;
a fourth cylindrical conductive band, positioned distal to the third cylindrical conductive band and arranged such that spacing between the third cylindrical conductive band and the fourth cylindrical conductive band defines a second spark gap, and a fourth wire electrically connecting the fourth cylindrical conductive band to the voltage source,
wherein when a voltage pulse is applied across the third and fourth wires, current will flow across the second spark gap and generate a shock wave in the liquid.

7. The catheter of claim 6, wherein a distal end of the third cylindrical conductive band comprises a circumferential side edge.

8. The catheter of claim 6, wherein a proximal end of the fourth cylindrical conductive band comprises a circumferential side edge.

9. The catheter of claim 6, wherein the distal end of the third cylindrical conductive band and the proximal end of the fourth cylindrical conductive band are located along the same cylindrical layer.

10. The catheter of claim 6, further comprising:
a fifth cylindrical conductive band, positioned distal to the fourth cylindrical conductive band, and a fifth wire electrically connecting the fifth cylindrical band to the voltage source;
a sixth cylindrical conductive band, positioned distal to the fifth cylindrical conductive band and arranged such that spacing between the fifth cylindrical conductive band and the sixth cylindrical conductive band defines a third spark gap, and a sixth wire electrically connecting the sixth cylindrical conductive band to the voltage source,
wherein when a voltage pulse is applied across the fifth and sixth wires, current will flow across the third spark gap and generate a shock wave in the liquid.

11. The catheter of claim 10, further comprising:
a seventh cylindrical conductive band, positioned distal to the sixth cylindrical conductive band, and a seventh wire electrically connecting the seventh cylindrical conductive band to the voltage source;
an eighth cylindrical conductive band, positioned distal to the seventh cylindrical conductive band and arranged such that spacing between the seventh cylindrical conductive band and the eighth cylindrical conductive band defines a fourth spark gap, and an eighth wire electrically connecting the eighth cylindrical conductive band to the voltage source,
wherein when a voltage pulse is applied across the seventh and eighth wires, current will flow across the fourth spark gap and generate a shock wave in the liquid.

12. A treatment catheter comprising:
an axially extending elongate member;
a first cylindrical conductive band mounted on the elongate member;
a second cylindrical conductive band mounted on the elongate member in a distal position relative to the first cylindrical conductive band, and arranged such that longitudinal spacing between the first cylindrical conductive band and the second cylindrical conductive band defines a first spark gap between the first and second cylindrical conductive bands;
a third cylindrical conductive band mounted on the elongate member in a distal position relative to the second cylindrical conductive band, and arranged such that longitudinal spacing between the second cylindrical conductive band and the third cylindrical conductive band defines a second spark gap between the second and third cylindrical conductive bands;
a first wire having a first end electrically connectable to a voltage source and having a second end in electrical communication with the first cylindrical conductive band;
a second wire having a first end electrically connectable to the voltage source and having a second end in electrical communication with the third cylindrical conductive band; and
a tube connected to the elongate member and surrounding the first, second, and third cylindrical bands, the tube being fillable with a conductive liquid, wherein the first, second, and third conductive bands are configured such that a voltage pulse applied across the first and second wires causes a current to flow across the first spark gap between the first and second cylindrical conductive bands and across the second spark gap between the second and third cylindrical conductive bands and generate shock waves in the liquid originating from the locations of both the first spark gap and the second spark gap.

13. The catheter of claim 12, wherein a distal end of the first cylindrical band and a proximal end of the second cylindrical band are located along the same cylindrical layer and the distal end of the second cylindrical band and the proximal end of the third cylindrical band are located along the same cylindrical layer.

14. The catheter of claim 12, wherein the any one or all of the first cylindrical band, the second cylindrical band, and the third cylindrical band are formed from a hypotube.

15. A treatment catheter comprising:
an axially extending elongate member;
a plurality of cylindrical conductive bands mounted to the elongate member and longitudinally spaced apart from each other; and
a plurality of wires electrically connecting a voltage source to the plurality of cylindrical conductive bands,
wherein the number of cylindrical conductive bands of the plurality of cylindrical conductive bands is n,
wherein the plurality of cylindrical conductive bands are spaced relative to one another to define at least one spark gap, wherein a number of spark gaps of the treatment catheter is n−1, and
wherein the plurality of cylindrical conductive bands are configured such that one or more voltage pulse applied to the plurality of wires causes current to flow across the at least one spark gap and generate at least one shock wave in the liquid.

16. The treatment catheter of claim 15, wherein n is an integer selected from 2, 4, 5, 7, 8, 10, 12, 16, and 20.

17. A treatment catheter comprising:
an axially extending elongate member;
a balloon;
a fluid lumen for introducing fluid to the balloon from a fluid source; and
an electrode pair comprising a first electrode and a second electrode and configured to generate a shock wave that propagates through the fluid and impinges on a calcified lesion,
wherein the first electrode is longitudinally spaced from the second electrode such that spacing between the first electrode and the second electrode forms a spark gap between the first electrode and the second electrode,
wherein the first electrode and the second electrode are circumferentially disposed around the axially extending elongate member,
wherein the treatment catheter is configured to facilitate navigation of the treatment catheter within tortuous vascular pathways, and
wherein the first electrode and the second electrode are configured such that a voltage pulse applied across the first electrode and the second electrode causes current to flow across the spark gap between the first electrode and the second electrode and generate a shock wave.

* * * * *